US010052412B2

(12) United States Patent
Arinzeh et al.

(10) Patent No.: US 10,052,412 B2
(45) Date of Patent: *Aug. 21, 2018

(54) ELECTROSPUN ELECTROACTIVE POLYMERS FOR REGENERATIVE MEDICINE APPLICATIONS

(71) Applicant: New Jersey Institute of Technology, Newark, NJ (US)

(72) Inventors: Treena L. Arinzeh, West Orange, NJ (US); Norbert Weber, Piscataway, NJ (US); Michael Jaffe, Maplewood, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/235,466

(22) Filed: Aug. 12, 2016

(65) Prior Publication Data

US 2017/0119931 A1 May 4, 2017

Related U.S. Application Data

(63) Continuation of application No. 12/411,320, filed on Mar. 25, 2009, now abandoned.

(60) Provisional application No. 61/039,214, filed on Mar. 25, 2008.

(51) Int. Cl.
  *C12N 5/00* (2006.01)
  *A61L 27/38* (2006.01)
  *A61L 27/16* (2006.01)
  *C12N 5/0793* (2010.01)

(52) U.S. Cl.
  CPC ........... *A61L 27/3895* (2013.01); *A61L 27/16* (2013.01); *A61L 27/383* (2013.01); *C12N 5/0068* (2013.01); *C12N 5/0619* (2013.01); *C12N 2501/13* (2013.01); *C12N 2506/1307* (2013.01); *C12N 2506/1353* (2013.01); *C12N 2533/30* (2013.01)

(58) Field of Classification Search
  CPC .... A61L 27/3895; A61L 27/16; A61L 27/383; C12N 5/0068; C12N 2501/13; C12N 2506/1353
  USPC ........................................................ 435/398
  See application file for complete search history.

(56) References Cited

U.S. PATENT DOCUMENTS

| | | |
|---|---|---|
| 4,846,835 A | 7/1989 | Grande |
| 5,030,225 A | 7/1991 | Aebischer et al. |
| 5,250,843 A | 10/1993 | Eichelberger |
| 5,353,498 A | 10/1994 | Fillion et al. |
| 5,486,359 A | 1/1996 | Caplan et al. |
| 5,626,861 A | 5/1997 | Laurencin et al. |
| 5,666,467 A | 9/1997 | Colak |
| 5,681,873 A | 10/1997 | Norton et al. |
| 5,766,618 A | 6/1998 | Laurencin et al. |
| 5,811,094 A | 9/1998 | Caplan |
| 5,827,735 A | 10/1998 | Young |
| 5,841,193 A | 11/1998 | Eichelberger |
| 5,906,934 A | 5/1999 | Grande et al. |
| 5,955,529 A | 9/1999 | Imai et al. |
| 6,095,148 A | 8/2000 | Shastri et al. |
| 6,165,486 A | 12/2000 | Marra et al. |
| 6,174,333 B1 | 1/2001 | Kadiyala |
| 6,214,369 B1 | 4/2001 | Grande et al. |
| 6,306,424 B1 | 10/2001 | Vyakarnam |
| 6,355,239 B1 | 3/2002 | Bruder |
| 6,387,367 B1 | 5/2002 | David-Sproul |
| 6,464,983 B1 | 10/2002 | Grotendorst |
| 6,472,210 B1 | 10/2002 | Holy et al. |
| 6,482,231 B1 | 11/2002 | Abatangelo |
| 6,489,165 B2 | 12/2002 | Bhatnager et al. |
| 6,511,511 B1 | 1/2003 | Slivka et al. |
| 6,541,024 B1 | 4/2003 | Kadiyala |
| 6,685,956 B2 | 2/2004 | Chu |
| 6,689,166 B2 | 2/2004 | Laurencin et al. |
| 6,689,374 B2 | 2/2004 | Chu |
| 6,730,252 B1 | 5/2004 | Teoh et al. |
| 6,783,712 B2 | 8/2004 | Slivka et al. |
| 6,790,455 B2 | 9/2004 | Chu |

(Continued)

FOREIGN PATENT DOCUMENTS

| | | | | |
|---|---|---|---|---|
| WO | WO2006068809 | * | 6/2006 | ............... H03L 7/00 |
| WO | WO 2006/095021 A1 | | 9/2006 | |
| WO | WO 2008/055038 A2 | | 5/2008 | |

OTHER PUBLICATIONS

Hardingham, Proteoglycans: Their Structure, Interactions and Molecular Organization in Cartilage, Biochemical Society Transactions, vol. 9, No. 6, pp. 489-497, 1981.

(Continued)

*Primary Examiner* — Julie Zhen Qin Wu
*Assistant Examiner* — Paul C Martin
(74) *Attorney, Agent, or Firm* — McCarter & English, LLP

(57) ABSTRACT

Due to the size and complexity of tissues such as the spinal cord and articular cartilage, specialized constructs incorporating cells as well as smart materials may be a promising strategy for achieving functional recovery. Aspects of the present invention describe the use of an electroactive, or piezoelectric, material that will act as a scaffold for stem cell induced tissue repair. Embodiments of the inventive material can also act alone as an electroactive scaffold for repairing tissues. The piezoelectric material of the present invention acts as a highly sensitive mechanoelectrical transducer that will generate charges in response to minute vibrational forces.

12 Claims, 7 Drawing Sheets

(56) References Cited

U.S. PATENT DOCUMENTS

| | | | |
|---|---|---|---|
| 6,790,528 | B2 | 9/2004 | Wendorff et al. |
| 6,863,900 | B2 | 3/2005 | Kadiyala |
| 7,012,106 | B2 | 3/2006 | Yuan et al. |
| 7,022,522 | B2 | 4/2006 | Guan et al. |
| 7,247,313 | B2 | 7/2007 | Roorda et al. |
| 7,271,234 | B2 | 9/2007 | Kohn et al. |
| 7,601,525 | B2 | 10/2009 | Batich et al. |
| 7,619,901 | B2 | 11/2009 | Eichelberger et al. |
| 7,767,221 | B2 | 8/2010 | Lu et al. |
| 7,803,574 | B2 | 9/2010 | Desai |
| 2002/0004039 | A1 | 1/2002 | Reid et al. |
| 2002/0173213 | A1 | 11/2002 | Chu et al. |
| 2003/0054035 | A1 | 3/2003 | Chu et al. |
| 2003/0069369 | A1 | 4/2003 | Belenkaya et al. |
| 2003/0077311 | A1 | 4/2003 | Vyakarnam et al. |
| 2003/0211130 | A1 | 11/2003 | Sanders et al. |
| 2004/0018226 | A1 | 1/2004 | Wnek et al. |
| 2005/0095695 | A1 | 5/2005 | Shindler et al. |
| 2005/0196423 | A1 | 9/2005 | Batich et al. |
| 2006/0057377 | A1* | 3/2006 | Harrison ............ B82Y 30/00 428/364 |
| 2006/0094320 | A1 | 5/2006 | Chen et al. |
| 2006/0128012 | A1 | 6/2006 | Arinzeh et al. |
| 2006/0198865 | A1 | 9/2006 | Freyman et al. |
| 2006/0204539 | A1 | 9/2006 | Atala et al. |
| 2006/0240064 | A9 | 10/2006 | Hunter et al. |
| 2007/0179594 | A1 | 8/2007 | Llanos et al. |
| 2007/0267725 | A1 | 11/2007 | Lee et al. |
| 2008/0009599 | A1 | 1/2008 | East et al. |
| 2008/0112150 | A1 | 5/2008 | Jones |
| 2008/0206343 | A1* | 8/2008 | Edinger ............ A01K 67/0271 424/489 |
| 2008/0246126 | A1 | 10/2008 | Bowles et al. |
| 2009/0028921 | A1 | 1/2009 | Arinzeh |
| 2009/0048358 | A1 | 2/2009 | Kim |
| 2009/0325296 | A1 | 12/2009 | Arinzeh et al. |
| 2010/0078771 | A1 | 4/2010 | Barth et al. |
| 2010/0078776 | A1 | 4/2010 | Barth et al. |
| 2010/0173158 | A1 | 7/2010 | Furuzono et al. |
| 2010/0233807 | A1 | 9/2010 | Arinzeh et al. |
| 2010/0324697 | A1 | 12/2010 | Arinzeh et al. |

OTHER PUBLICATIONS

Davis, et al., Structural and Dielectric Investigation on the Nature of the Transition in a Copolymer of Vinylidene Fluoride and Trifluoroethylene, Macromolecules, 15: 329-333, 1982.

Lovinger, Ferroelectric Polymers, Science, New Series, vol. 220, No. 4602, pp. 1115-1121, 1983.

Petel, et al., Perturbation of the Direction of Neurite Growth by Pulsed and Focal Electric Fields, Journal of Neurosci, vol. 4, pp. 2939-2947, 1984.

Humphrey, et al., The Dielectric Piezoelectric and Pyroelectric Properties of VDF-TrFE Copolymers, Plessey Research (Caswell) Limited, Allen Clark Research Centre, Caswell, Towcester, Northants, NN12 8EQ, England, 1986.

Friedenstein, A. et al., Bone Marrow Osteogenetic Stem Cells: In Vitro Cultivation and Transplantation in Diffusion Chambers, Cell Tissue Kinet, 1987, 20(3):263-72.

Borgens, Electric Fields in Vertebrate Repair, Natural and Applied Voltage in Vertebrate Regeneration and Hearling, Wiley-Liss, 1989.

Sambrook et al., Molecular Cloning: A Laboratory Manual, 2nd 3d., Cold Spring Harbor Laboratory, Cold Spring Harbor Laboratory Press, Cold Spring Harbor, NY, 1989. (cover page and Table of Contents for vols. 1-3).

Koga, et al., Crystallization, Field-Induced Phase Transformation, Thermally Induced Phase Transition, and Piezoelectric Activity in P(Vinylidene Fluoride-TrFE) Copolymers with High Molar Content of Vinylidene Fluoride, J. Appl. Phys, 67(2), pp. 965-974, 1990.

Safronova, et al., Characteristics of the Macromolecular Components of the Extracellular Matrix in Human Hyaline Cartilage at Different Stages of Ontogenesis, Biomedical Science, 2:162-168, 1991.

Haynesworth, S. et al., Cell Surface Antigens on Human Marrow-Derived Mesenchymal Stem Cells are Detected by Monoclonal Antibodies, J. Cell Physiol., 1992, 138:8-16.

Valentini, Electrically Charged Polymeric Substrates Enhance Nerve-Fiber Outgrowth in Vitro, Biomaterials, vol. 13, pp. 183-190, 1992.

Ausubel, et al., Current Protocols in Molecular Biology, John Wiley & Sons, New York, NY, 1993. (cover page and Table of Contents).

Rickard, D. J. et al., Induction of rapid osteoblast differentiation in rat bone marrow stromal cell cultures by dexamethason and BMP-2, Dev. Bio., 1994, 161:218-28.

Ohigashi, et al., Formation of "Single Crystalline Films" of Ferroelectric Copolymers of Vinylidene Fluoride and Trifluoroethylene, Appl. Phys. Lett., 66(24), pp. 3281-3283, 1995.

Kapur, et al, Human Monocyte Morphology is Affected by Local Substrate Charge Heterogeneity, Journal of Biomed Mater. Res., 32: 133, 1996 (abstract only).

Kapur., et al., Fabrication and Selective Surface Modification of 3-Dimensionally Textured Biomedical Polymers from Etched Silicon Substrates, Journal of Biomedical Materials Research, vol. 33, pp. 205-216 (1996).

Bouaziz, et al., Vascular Endothelial Cell Responses to Different Electrically Charged Poly(Vinylidene Fluoride) Supports Under Static and Oscillating Flow Conditions, Biomaterials, vol. 18, No. 2, 107-112, 1997.

Christie, et al., Ferroelectric and Piezoelectric Properties of a Quenched Poly(Vinylidene Fluoride-Trifluoroethylene) Copolymer, Journal of Polymer Science: Part B: Polymer Physics, vol. 35, 2671-2679, 1997.

Furukawa, Structure and Functional Properties of Ferroelectric Polymers, Advances in Colloid and Interface Science, 71-72; 183-208, 1997.

Jaiswal, N. et al., Osteogenic differentiation of purified culture-expanded human mesenchymal stem cells in vitro, J. Cell Biochem., 1997, 64:295-312.

Kadiyala, S. et al., Culture-expanded, bone marrow-derived mesenchymal stem cells can regenerate a critical-sized segmental bone defect, Tissue Engineering, 1997, 3(2):173-185.

Miraglia, S. "A Novel Five-Transmembrane Hematopoietic Stem Cell Antigen: Isolation, Characterization, and Molecular Cloning," *Blood* 90:5013-21 (1997).

Omote, et al., Temperature Dependence of Elastic, Dielectric, and Piezoelectric Properties of "Single Crystalline" Films of Vinylidene Fluoride Trifluoroethylene Copolymer, J. Appl. Phys., 81(6), pp. 2760-2769, 1997.

Schmidt, et al., Stimulation of Neurite Outgrowth Using an Electrically Conducting Polymer, Proc. Natl. Acad. Sci, vol. 94, pp. 8948-8953, 1997.

Virts, E. et al. "Murine Mast Cells and Monocytes Express Distinctive Sets of CD45 Isoforms," *Immunology* 34(16-17):1119-97 (1997).

Yin, A.H. "AC133, A Novel Marker for Human Hematopoietic Stem and Progenitor Cells," *Blood* 90:5002-12 (1997).

Brudner, S. P. et al., Bone Regeneration by Implantation of Purified, Culture-Expanded Human Mesenchymal Stem Cells, J. Orthop. Res., 1998, 16:155-162.

Bune, et al., Two-Dimensional Ferroelectric Films, Nature, vol. 391, 874-877, 1998.

Mackay, A. M. et al., Chrondrogenic differentiation of cultured human mesenchymal stem cells from marrow, Tissue Engineering, 1998, 4(4):415-428.

Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.

Borgens, Electrically Mediated Regeneration and Guidance of Adult Mammalian Spinal Axons into Polymeric Channels, Neuroscience, 91(1):251-64; 1999.

Laurencin, C.T. "Tissue Engineering: Orthopedic Applications," *Ann. Rev. Biomed. Eng'g* 1:19-46 (1999).

Pittenger, M. F. et al., Multilineage potential of adult human mesenchymal stem cells, Science, 1999, 284:143-7.

Praemer, A., Musculoskeletal conditions in the United States, American Academy of Orthopaedic Surgeons, 1999, p. 34-39.

(56) References Cited

OTHER PUBLICATIONS

Sittinger et al., Joint cartilage regeneration by tissue engineering, Z. Rheumatol, 58:130-5, 1999.
Browne, J. E. et al., Surgical alternatives for treatment of articular cartilage lesions, J. Am. Acad. Orthop. Surg., 2000, 8(3):180-9.
DeLise, et al., Cellular Interactions and Signaling in Cartilage Development, Osteoarthritis and Cartilage, 8: 309-334, 2000.
Fuchs, et al., Stem Cells: A New Lease on Life, Cell 100: 143-155, 2000.
Hilczer, et al., The Method of Matching Resonance Frequencies in Coupled Transmitter PVDF/TRFE Diaphragms, IEEE Transactions on Dielectrics and Electrical Insulation, vol. 7, No. 4, pp. 498-502, 2000.
Ponticello, et al., Gelatin-Based Resorbable Spone as a Carrier Matrix for Human Mesenchymal Stem Cells in Cartilage Regeneration Therapy, J. Biomed Materials Res., 52:246-255, 2000.
Watt, et al., Out of Eden: Stem Cells and Their Niches, Science, 287:1427-1430, 2000.
Xie, et al., A Niche Maintaining Germ Line Stem Cells in *Drosophila* Ovary, Science 290:328, 2000.
Barry, et al., Chondrogenic Differentiation of Mesenchymal Stem Cells from Bone Marrow: Differentiation-Dependent Gene Expression of Matrix Components, Experimental Cell Research, 268:189-200 (2001).
Brook, et al., Columns of Schwann Cells Extruded into the CNS Induce In-Growth of Astrocytes to Form Organized New Glial Pathways, Glia, 33:118-130, 2001.
Christensen, N. D. et al., Papillomavirus microbicidal activities of high-molecular-weight cellulose sulfate, dextran sulfate, and polystyrene sulfonate, Antimicrobial Agents and Chemotherapy, 2001, 45(12):3427-32.
Guo et al., Biological features of mesenchymal stem cells from human bone marrow, Chinese Med J.. 114:950-3, 2001.
Harrison, et al., Piezolelectric Polymers, ICASE, NASA Langley Research Center, Hampton, Virginia, NASA/CR-2001-211422, ICASE Report No. 2001-43, pp. 1-26, 2001.
Ishihara, M. et al., Heparin-carrying polystyrene (HCPS)-bound collagen substratum to immobilize heparin-binding growth factors and to enhance cellular growth, J. Biomed. Mat. Res., 2001, 56(4):536-44.
Koombhongse, et al., Flat Polymer Ribbons and Other Shapes by Electrospinning, Journal of Polymer Science: Part B: Polymer Physics, vol. 39, 2598-2606, 2001.
Kotwal, et al., Electrical Stimulation Alters Protein Adsorption and Nerve Cell Interactions With Electrically Conducting Biomaterials, Biomaterials, 22: 1055-1064, 2001.
Negishi, Optic Nerve Regeneration Within Artificial Schwann Cell Graft in the Adult Rat, Brain Research Bulletin, 55:409-419, 2001.
N.S.C.I.A., Spinal Cord Injury Fact Sheet, Birmingham, 2001; http://users.erols.com/nscia/resource/factshts/.
Ploss, et al., Poling Study of PZT/P(VDF-TrFE) Composites, Composites Science and Technology, 61, 957-962, 2001.
Rahman et al., Enhancement of Chondrogenic Differentiation of Human Articular Chondrocytes by Biodegradable Polymers, Tissue Engineering, 7:781-90, 2001.
Rogovina, S. Z. et al., Solid state production of cellulose-chitosan blends and their modification and the diglycidyl ether of oligo(ethylene oxide), Polymer Degradation and Stability, 2001, 73(3):557-60.
Yannas IV, Tissue and Organ Regeneration in Adults, Springer, 2001(cover page and Table of Contents).
Anderson, R. A. et al., Preclinical evaluation of sodium cellulose sulfate (Ushercell) as a contraceptive antimicrobial agent, Journal of Andrology, 2002, 23(3):426-38.
Arinzeh, T. et al.,In vivo evaluation of a bioactive scaffold for bone tissue engineering, J. Biomed. Mat. Res., 2002, 62:1-13.
Dozin, B. et al., Response of young, aged and osteoarthritic human articular chondrocytes to inflammatory cytokines: molecular and cellular aspects, Matrix Biology, 2002, 21(5):449-59.

Li, Wan-Ju et al., Electrospun Nanofibrous Structure: A Novel Scaffold for Tissue Engineering, Journal of Biomedical Materials Research, vol. 60, No. 4, pp. 613-621, 2002.
Mueller, et al., Processing of Gene Expression Data Generated by Quantitative Real-Time RT-PCR, BioTechniques, 32: No. 6, 2-7 (2002).
Muller, P. Y. et al., Processing of gene expression data generated by quantitative real-time RT-PCR, Biotechniques, 2002, 32(6):1372-4.
Nettles et al., Potential Use of Chitosan as a Cell Scaffold Material for Carilage Tissue Engineering, Tissue Engineering, Vo.. 8, No. 6, pp. 1009-1016, 2002.
Arinzeh, T. et al, Allogeneic mesenchymal stem cells regenerate bone in a critical-sized canine segmental defect, Journal of Bone and Joint Surgery American, 2003, 85-A(1):1927-35.
Benz, et al., Determination of the Crystalline Phases of Poly(Vinylidene Fluoride) Under Different Preparation Conditions Using Differential Scanning Calorimetry and Infrared Spectroscopy, Journal of Applied Polymer Science, vol. 89, 1093-1100, 2003.
Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.
Li, et al., Biological Response of Chondrocytes Cultured in Three-Dimensional Nanofibrous Poly(e-caprolactone) Scaffolds, J. Biomed. Mater. Res. 67A: 1105-1114 (2003).
Livingston, et al., Mesenchymal Stem Cells Combined With Biphasic Calcium Phosphate Ceramics Promote Bone Regeneration, Journal of Materials Science: Materials in Medicine, 14: 211-218 (2003).
Luu et al., "Development of a Nanostructured DNA Delivery Scaffold via Electrospinning of PLGA and PLA-PEG block copolymers". Journal of Controlled Release, 2003, vol. 89, pp. 341-353.
Murphy, et al., Stem Cell Therapy in a Caprine Model of Osteoarthritis, Arthritis Rheumatism, 48: 3464-3474, 2003.
Sachlos, et al., Making Tissue Engineering Scaffolds Work, Review of the Application of Solid Freeform Fabrication Technology to the Production of Tissue Engineering Scaffolds, *European Cells & Materials* 5: 29-40 (2003).
Seoul, et al., Electrospinning of Poly(Vinylidene Fluoride)/Dimethylformamide Solutions With Carbon Nanotubes, Journal of Polymer Science: part B: Polymer Physics, vol. 41, 1572-1577, 2003.
Sikavitsas et al., "Mineralized Matrix Deposition by Marrow Stromal Osteoblasts in 3D Perfusion Culture Increases With Increasing Fluid Shear Forces". PNAS, Dec. 9, 2003, vol. 100, No. 25, pp. 14683-14688.
Wan-Ju, et al., Biological Response of Chondrocytes Cultrued in Three-Dimensional Nanofibrous Poly(€-caprolactone) Scaffolds, J. Biomed. Mater. Res. 67A:1105-1114, 2003.
Yeh, E.T.H. et al., "Transdifferentiation of Human Peripheral Blood CD34+-Enriched Cell Population Into Cardiomyocytes, Endothelial Cells, and Smooth Muscle Cells in Vivo," Circulation 108:2070-73, 2003.
Yoshimoto et al., A Biodegradable Nanofiber Scaffold by Electrospinning and its Potential for Bone Tissue Engineering, Biomaterials, 24, pp. 2077-2082, 2003.
Zong et al., Electrospun Non-woven Membranes as Scaffolds for Heart Tissue Constructs. 226th ACS National Meeting, 2003.2003.
Bhattarai, et al., Novel Biodegradable Electrospun Membrane: Scaffold for Tissue Engineering, Biomaterials, vol. 25, No. 13, pp. 2595-2602, 2004.
Bryan, et al., Enhanced Peripheral Nerve Regeneration Through a Poled Bioresorbable Poly(Lactic-co-glycolic Acid) Guidance Channel, J. Neural Eng., 1, 91-98, 2004.
Chen, et al., Chondrogenic differentiation of human mesenchymal stem cells cultured in a cobweb-like biodegradable scaffold, Biochemical and Biophysical Research Communications, 322, pp. 50-55 (2004).
Desawa, M., Specific Induction of Neuronal Cells From Bone Marrow Stromal Cells and Application for Autologous Transplantation, Journal of Clinical Investigation; 113:1701-1710, 2004.

(56) References Cited

OTHER PUBLICATIONS

Jin et al., "Human Bone Marrow Stromal Cell Responses on Electrospun Silk Fibroin Mats", Biomaterials, 2004, vol. 25, pp. 1039-1047.
Li et al., Carbon Nanotubes Induced Nonisothermal Crystallization of Ethylene-Vinyl Acetate Copolymer, Materials Letter, 58, pp. 3967-3970, 2004.
Rosenzweig, et al., Rodent Models for Treatment of Spinal Cord Injury: Research Trends and Progress Toward Useful Repair, Current Opinion in Neurology, 17(2); 121-31, 2004.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.
Shields, K. J. et al., Mechanical properties and cellular proliferation of electrospun collagen Type II, Tissue Engineering, 2004, 10(9-10):1510-7.
Shin et al., In Vivo Bone Tissue Engineering Using Mesenchymal Stem Cells on a Novel Electrospun Nanofibrous Scaffold, Tissue Engineering, 10, pp. 33-41, 2004.
Sittinger et all., Current Strategies for Cell Delivery in Cartilage and Bone Regeneration, Current Opinion in Biotechnology, vol. 115, Issue 5, pp. 411-418, 2004.
Wei et al., Structural and Properties of Nano-Hydroxyapatite/Polymer Composite Scaffolds for Bone Tissue Engineering, Biomaterials, 25, pp. 4749-4757, 2004.
You, J. O. et al., Calcium-alginate nanoparticles formed by reverse microemulsion as gene carriers, macromolecular Symposia, 2004, 219(147):153.
Arinzeh, T.L., et al., A comparative study of biphasic calcium phosphate ceramics for human mesenchymal stem-cell-induced bone formation, Biomaterials 26(17), pp. 3631-3638, 2005.
Aroen, A. et al, "Articular Cartilage Defects in a Rabbit Model, Retention Rate of Periosteal Flap Cover", Acta Orthrop. 76(2):220-4, 2005.
Browne, J. E. et al., Clinical outcome of autologous chondrocyte implantation at 5 years in US subjects, Clinical Orthopaedics and Related Research, 2005, 436:237-45.
Clar, C. et al., Clinical and cost-effectiveness of autologous chondocyte implantation for cartilage defects in knee joints: systematic review and economic evaluation, Health Technology Assessment, 2005, 9(47):four pages.
Cummings, et al., Human Neural Stem Cells Differentiate and Promote Locomoter Recovery in Spinal Cord-Injured Mice, Proceedings of the National Academy of Sciences, 102(39):14069-74, 2005.
Ducharme, et al., Ferroelectric Polymeric Langmuir-Blodgett Films for Non-Volatile Memory Applications, Nebraska Research Initiative, the National Science Foundation and the Office of Naval Research, Department of Physics and Astronomy and the Center for Materials Research and Analysis at the University of Nebraska, Lincoln, NE, pp. 1-41, 2005.
Fujihara, et al., Guided Bone Regeneration Membrane Made of Polycaprolactone/Calcium Carbonate Composite Nano-fibers, Biomaterials, 26, pp. 4139-4147, 2005.
Holmes, N. "CD45: All is Not Yet Crystal Clear", Immunology 117:145-155, 2005.
Kang, S. W. et al., Ply(lactic-co-glycolic acid) microspheres as an injectible scaffold for cartilage tissue engineering, Tissue Engineering, 2005, 11(3-4):438-47.
Klein, et al., Influence of Composition on Relaxor Ferroelectric and Electromechanical Properties of Poly(Vinyliden Fluoride-Trifluoroethylene-Chlorofluoroethylene), Journal of Applied Physics, 97, 094105, pp. 1-4, 2005.
Laxminarayana, et al., Functional Nanotube-Based Textiles: Pathyway to Next Generation Fabrics With Enhanced Sensing Capabilities, Textile Res. J., 75(9), 670-680, 2005.
Li, Wan-Ju et al., Multilineage Differentiation of Human Mesenchymal Stem Cells in a Three-Dimensional Nanofibrous Scaffold, Biomaterials, vol. 26, No. 25, pp. 5158-5166, 2005.
Maire, M. et al., Retention of transforming growth factor using functionalized dextran-based hydrogels, Biomaterials, 2005, 26(14):1771-80.
Montjovent et al., Biocompatibility of Bioresorbable Poly(L-lactic acid) Composite Scaffolds Obtained by Supercritical Gas Foaming With Human Fetal Bone Cells, Tissue Engineering 11, pp. 1640-1649, 2005.
Naber, et al., Low-Voltage Programmable Ferroelectric Polymer Field-Effect Transistors, Applied Physics Letters, 87: 203509, pp. 51-57, 2005.
Nasir, et al., Control of Diameter, Morphology, and Structure of PVDF Nanofiber Fabricated by Electrospray Deposition, Journal of Polymer Science: Part B: Polymer Physics, vol. 44, 779-786, 2006.
Schaffellner, S. et al., Porcine islet cells microencapsulated in sodium cellulose sulfate, Transplantation Proceedings, 2005, 37(1):248-52.
Shapiro, et al., Oscillating Field Stimulation for Complete Spinal Cord Injury in Humans: A Phase 1 Trial, Journal of Neurosurgery Spine, 2005:2(1):3-10.
Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 1881-1891, 2005.
Wutticharoenmongkol, Preparation and Characterization of Novel Bone Scaffolds Based on Electrospun Polycaprolactone Fibers Filled with Nanoparticles, Macromolecular Bioscience, vol. 6, pp. 70-77, 2005.
Zhang et al., Tissue-Engineering Approaches for Axonal Guidance, Brain Res. Brain Res. Rev, vol. 49, pp. 48-64, 2005.
Zhao, et al., Preparation and Properties of Electrospun Poly(Vinylidene Fluoride) Membranes, Journal of Applied Polymer Science, vol. 97, 466-474, 2005.
Beloti, et al., In Vitro Biocompatibility of a Novel Membrane of the Composite Poly(Vinylidene-Trifluoroethylene)/Barium Titanate, InterScience Journal of Biomedical Materials Research Part A, 281-288, 2006.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Gama, C. L., Sulfation patterns of glycosaminoglycans encode molecular recognition and activity, Nature Chemical Biology, 2006, 2(9):467-73.
Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.
Himes, et al., Recovery of Function Following Grafting of Human Bone Marrow-Derived Stromal Cells Into the Injured Spinal Cord, Neurorehabilitation and Neural Repair, 20:278-96, 2006.
Hung, et al., The Effect of Chitosan and PVDF Substrates on the Behavior of Embryonic Rat Cerebral Cortical Stem Cells, Biomaterials, 27, 4461-4469, 2006.
Kuo, C. K. et al., Cartilage tissue engineering: its potential and uses, Current Opinion in Rheumatology, 2006, 18(1):64-73.
Li, W. J. et al., Fabrication and characterization of six electrospun poly(alpha-hydroxyester)-based fibrous scaffolds for tissue engineering applications, Acta Biomaterialia, 2006, 2(4):377-85.
Oudega, et al., Schwann Cell Transplantation for Repair of the Adult Spinal Cord, Journal of Neurotrauma, 23(3-4), 453-67, 2006.
Pelttari, K. et al., Premature induction of hypertrophy during in vitro chondrogenesis of human mesenchymal stem cells correlates with calcification and vascular invasion after ectopic transplantation in SCID mice, Arthritis and Rheumatism, 2006, 54:3254-66.
Rezwan et al., Biodegradable and Bioactive Porous Polymer/inorganic Composite Scaffolds for Bone Tissue Engineering, Biomaterials, 27, pp. 3413-3431, 2006.
Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.
Stiegler, P. B. et al., Cryopreservation of insulin-producing cells microencapsulated in sodium cellulose sulfate, Transplantation Proceedings, 2006, 38(9):3026-30.

(56) References Cited

OTHER PUBLICATIONS

Tashiro, et al, Structural Correlation Between Crystal Lattice and Lamellar Morphology in the Ferroelectric Phase Transition of Vinylidene Fluoride-Trifluoroethylene Copolymers as Revealed by the Simultaneous Measurements of Wide-Angle and Small-Angle X-Ray Scatterings, Polymer, 47, 5433-5444, 2006.
Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487-493, 2006.
Wu, et al., Poly(Vinylidene Fluoride)/Polyethersulfone Blend Membranes: Effects of Solvent Sort, Polyethersulfone and Polyvinylpyrrolidone Concentration on Their Properties and Morphology, Journal of Membrane Science, 285, 290-298, 2006.
Wutticharoenmongkol, et al., Novel Bone Scaffolds of Electrospun Polycaprolactone Fibers Filled With Nanoparticles, Journal of Nanoscience Nanotechnology, 6(2), pp. 514-522, 2006.
Wutticharoenmongkol et al., Preparation and Characterization of Novel Bone Scaffolds Based on Electrospun Polycaprolactone Fibers Filled with Nanoparticles, Macromol. Biosci. 6, pp. 70-77, 2006.
Yang, et al., Preparation of Bioelectret Collagen and Its Influence on Cell Culture In Vitro, J. Mater. Sci: Mater Med, 17:767-771, 2006.
Catalani, et al., Evidence for Molecular Orientation and Residual Charge in the Electrospinning of Poly(Butylenes Terephthalate) Nanofibers, Macromolecules, vol. 40, pp. 1693-1697, 2007.
Chamberlain, G. et al., Concise review: mesenchymal stem cells: their phenotype, differentiation capacity, immunological features, and potential for homing, Stem Cells, 2007, 25(11):2739-49.
Collins, M. N. et al., Comparison of the effectiveness of four different crosslinking agents with hyaluronic acid hydrogel films for tissue-culture applications, Journal of Applied Polymer Science 2007, 104(5):3183-91.
Greco, S. et al., An interdisciplinary approach and characterization of neuronal cells transdifferentiated from human mesenchymal stem cells, Stem cells and development, 2007, 16(5):811-26.
Greco, S. J. et al., Functional similarities among genes regulated by oct-4 in human mesenchymal and embryonic stem cells, Stem Cells, 2007, 25(12:3143-54.
Greiner, et al, Electrospinning: A Fascinating Method for the Preparation of Ultrathin Fibers, Angewandte Chemie Int. Ed. Engl. 46: 5670-5703 (2007).
Huang, Isothermal Crystallization of High-Density Polyethylene and Nanoscale Calcium Carbonate Composites, Journal of Applied Science, 107, pp. 3163-3172, 2007.
Karlsson, C. et al., Differentiation of human mesenchymal stem cells and articular chondrocytes: analysis of chondrogenic potential and expression pattern of differentiation-related transcription factors, Journal of Orthopaedic Research, 2007, 25:152-63.
Lack, S. et al., High-resolution nuclear magnetic resonance spectroscopy studies of polysaccharides crosslinked by sodium trimetaphosphate: a proposal for the reaction mechanism, Carbohydrate Research, 2007, 342(7):943-53.
Miyazaki, et al., Crystallization Rate of Amorphous Nifedipine Analogues Unrelated to the Glass Transition Temperature, International Journal of Pharmaeceutics, 336, pp. 191-195, 2007.
Osiris Therapeutics Announces Positive One Year Data from Chondrogen Trial for Knee Repair, Osiris Therapeutics, Inc., Ref. Type: Internet Communication, 2007.
http://stemcells.nih.gov/info/scireport/appendixE.asp, (visited Dec. 28, 2007; last visited Aug. 25, 2011), 6 pages.
http://stemcells.nih.gov/info/scireport/appendixE.asp, (visited Dec. 28, 2007).
Sun, et al. Crystallization and Thermal Properties of Polyamide 6 Composites Filled With Different Nanofillers, Materials Letters, 61, pp. 3963-3966, 2007.
Temple, M. M. et al., Age- and site-associate biomechanical weakening of human articular cartilage of the femoral condyle, Osteoarthritis and Cartilage, 2007, 15:1042-52.
Venugopal et al., Biocomposite Nanofibres and Osteoblasts for Bone Tissue Engineering, Nanotechnology, 18, pp. 1-8, 2007.
Wi, et al., Characterization of Poly(Vinylidene Fluoride-Trifluoroethylene) 50/50 Copolymer Films as a Gate Dielectric, J. Mater Sci: Mater Electron, pp. 1-6, 2007.
Xin, X. et al., Continuing differentiation of human mesenchymal stem cells and induced chondrogenic and osteogenic lineages in electrospun PLGA nanofiber scaffold, Biomaterials, 2007, 28(2):316-25.
Zhou et al., In Vitro Bone Engineering Based on Polycaprolactone and Polycaprolactone-Tricalcium Phosphate Composites, Polym. Int. 56, pp. 333-342, 2007.
Bian, L. et al., Influence of chondoitin sulfate on the biochemical, mechanical and frictional properties of cartilage explants in long-term culture, Journal of Biomechanics, in press 2008.
Chen, Y. et al., Development of a chitosan-based nanoparticle formulation for delivery of a hydrophilic hexapeptide, dalargin, Biopolymers, 2008, 90(5):663-70.
Chondrogen clinical trial information for the treatment of knee injuries, Osiris Therapeutics, Inc., 2008, Ref. Type: Internet Communication.
Duffell., et al., Long-Term Intensive Electrically Stimulated Cycling by Spinal Cord-Injured People: Effect on Muscle Properties and Their Relation to Power Output, Muscle and Nerve, 2008, 38:1304-11.
Forsten-Williams, K., et al., Control of growth factor networks by heparin sulfate proteoglycans, Annals of Biomedical Engineering, 2008, 36(12):2134-48.
Kim, et al., The Role of Aligned Polymer Fiber-Based Constructs in the Bridging of Long Peripheral Nerve Gaps, Biomaterials, 29(21):3117-27, 2008.
Lankford, et al., Olfactory Ensheathing Cells Exhibit Unique Migratory, Phagocytic and Myelinating Properties in the X-Irradiated Spinal Cord Not Shared by Schwann Cells, Glia, 2008; epub ahead of print.
Liu, Z. et al., Polysaccharides-based nanoparticles as drug delivery systems, Advanced Drug Delivery Reviews, 2008, 60(15):1650-62.
Magnussen, R. A. et al., Treatment of focal articular cartilage defects in the knee: a systematic review, Clinical Orthopaedics and Related Research, 2008, 466(4):952-62.
Mueller, M. B. et al., Functional characterization of hypertrophy in chondrogenesis of human mesenchymal stem cells, Arthritis and Rheumatism, 2008, 58(5):1377-88.
European Search Report dated Dec. 9, 2009.
PCT International Preliminary Report on Patentability from PCT/US2008/067322 filed Jun. 18, 2008 (WO2008/157594) dated Dec. 22, 2009.
PCT International Search Report and Written Opinion for PCT/US2005/043876 dated Jun. 25, 2008.
PCT International Search Report and Written Opinion for PCT/US2008/067322 dated Sep. 29, 2008.
ISP Dec. 24, 2008 for PCT/US2008/067322. International Publication No. WO 2008/157594.
European Search Report dated Dec. 9, 2009 for PCT/US2005/043876.
IPRP Dec. 22, 2009 for PCT/US2008/067322.
Shanmugasundaram, S. et al., Regulation of human mesenchymal stem cell chondrogenesis by scaffold geometry and mechanical properties, Society for Biomaterials Annual Meeting, 2009.
Shanmugasundaram, et al., Microscale Versus Nanoscale Scaffold Architecture for Mesenchymal Stem Cell Chondrogenesis, Tissue Engineering: Part A, vol. 60, No. 00, 2010, pp. 1-10.
PCT International Search Report and Written Opinion for PCT/US2012/050156 dated Feb. 1, 2013.
European Patent Office Action for European Patent Application No. 05852938.9 dated Jul. 1, 2014.
U.S. Appl. No. 11/291,701, filed Dec. 1, 2005, 2006/0128012.
U.S. Appl. No. 12/141,340, filed Jun. 18, 2008, 2009/0028921.
U.S. Appl. No. 12/411,320, filed Mar. 29, 2009, 2009/0325296.
U.S. Appl. No. 12/661,242, filed Mar. 12, 2010, 2010/0233234.
U.S. Appl. No. 12/661,264, filed Mar. 12, 2010, 2010/0324697.
U.S. Appl. No. 12/763,755, filed Apr. 20, 2010, 2010/0233807.
U.S. Appl. No. 13/097,657, filed Apr. 29, 2011, 2010/0274742.

(56) References Cited

OTHER PUBLICATIONS

U.S. Appl. No. 13/210,806, filed Aug. 16, 2011, 2011/0300626.
U.S. Appl. No. 13/651,296, filed Oct. 12, 2012, 2013/0052254.
U.S. Appl. No. 14/381,496, filed Aug. 27, 2014.
PCT/US2005/043876, Dec. 1, 2005, WO 2006/068809.
PCT/US2008/067322, Jun. 18, 2008, WO 2005/157594.
PCT/US2012/050156, Aug. 9, 2012, WO 2013/023064.
U.S. Appl. No. 61/039,214, filed Mar. 25, 2008.

* cited by examiner

ELECTROSPUN ELECTROACTIVE POLYMERS FOR REGENERATIVE MEDICINE APPLICATIONS

CROSS-REFERENCE TO RELATED APPLICATIONS

This application is a continuation patent application that claims priority benefit to a co-pending non-provisional patent application entitled "Electrospun Electroactive Polymers for Regenerative Medicine Applications," which was filed on Mar. 25, 2009, and assigned Ser. No. 12/411,320, now abandoned, which in turn claims the benefit of U.S. Provisional Patent Application Ser. No. 61/039,214 filed Mar. 25, 2008, entitled "Electrospun Electroactive Polymer for Regenerative Medicine Applications", each of which is herein incorporated by reference in its entirety.

FIELD OF THE INVENTION

The present invention relates to the use of a synthetic electroactive, or piezoelectric, biomaterial useful as an electroactive scaffold for repairing tissues. The scaffold may be used alone or in combination with cells as scaffold for tissue repair or regeneration.

BACKGROUND OF THE INVENTION

Tissue engineering is the application of principles and methods of engineering and life sciences toward a fundamental understanding and development of biological substitutes to restore, maintain and improve human tissue functions.

Orthopedic management of lesions to articular cartilage remains a persistent problem for the orthopedist and patient because articular cartilage has a limited intrinsic ability to heal. This has prompted the development of numerous procedures to treat these lesions and to halt or slow the progression to diffuse arthritic changes.

Tissue engineering may eliminate many of the problems associated with current surgical options. Current tissue engineering methods are aimed at filling the cartilage defects with cells with or without scaffolds to promote cartilage regeneration. Implantation of scaffolds alone leads to a poor quality reparative tissue. Chondrocytes implanted either alone or in combination with a scaffold have failed to restore a normal articular surface, and the hyaline cartilage formed early on in response to chondrocyte-containing scaffolds seems to deteriorate with time.

Damage to the spinal cord may result in autonomic dysfunction, a loss of sensation, or a loss of mobility. Such spinal cord injury (SCI) frequently is caused by trauma, tumors; ischemia, developmental disorders, neurodegenerative diseases, demyelinative diseases, transverse myelitis, vascular malformations, or other causes. The consequences of SCI depend on the specific nature of the injury and its location along the spinal cord. In addition because SCI is a dynamic process, the full extent of injury may not be apparent initially in all acute cord syndromes. Incomplete cord lesions may evolve into more complete lesions; more commonly, the injury level rises one or two spinal levels during the hours to days after the initial event. A complex cascade of pathophysiologic events accounts for this clinical deterioration.

The psychological and social impact of SCIs often is devastating. Some of the general disabling conditions associated with SCI are permanent paralysis of the limbs, chronic pain, muscular atrophy, loss of voluntary control over bladder and bowel, sexual dysfunction, and infertility.

Recent advances in neuroscience have drawn considerable attention to research into SCI and have made significantly better treatment and rehabilitation options available. Functional electrical stimulation (FES), for example, has shown the potential to enhance nerve regeneration and allow significant improvements in restoring and improving functional capacity after SCI. However, not all patients with spinal cord injury qualify for FES (a complete lesion of the spinal cord must be established); the patient must be in a neurologically stable condition; and the peripheral nerves must be intact to respond to exogenous electrical stimulations. Therefore, tissue engineering methods that could successfully restore, maintain, and improve the damage caused by spinal cord injury would eliminate many of the problems associated with current treatment options.

The development of improved tissue regeneration strategies will require a multi-disciplinary approach combining several technologies. Due to the size and complexity of tissues such as the spinal cord and articular cartilage, specialized constructs incorporating cells as well as smart materials may be a promising strategy for achieving functional recovery.

The use of stem cells for tissue engineering therapies is at the forefront of scientific investigation. Stem cells have the ability to differentiate into various cells types and thus promote the regeneration or repair of a diseased or damaged tissue of interest.

For example, mesenchymal stem cells (MSC) are multipotent cells that are capable of differentiating along several lineage pathways. In the body, adult stem cells often are localized to specific chemically and topologically complex microenvironments, or so-called "niches". Increasing experimental evidence supports the notion that stem cells can adjust their properties according to their surroundings and select specific lineages according to cues they receive from their niche (Xie L, Spradling, A C, "A Niche Maintaining Germ Line Stem Cells In Drosophila Ovary," *Science* 290:328 (2000); Fuchs E, Segre J, "Stem Cells: A New Lease On Life," *Cell* 100: 143-155 (2000), Watt F M, Hogan B L M, "Out Of Eden: Stem Cells And Their Niches," *Science* 287:1427 (2000)). It follows that in order for an MSC therapy to be successful in the repair of a specific tissue type, the microenvironment of the cells should be designed to relay the appropriate chemical and physical signals to them.

A viable approach may be to mimic characteristics of the microenvironment during cartilage and neurite development may be a viable approach. During cartilage development, for example, one of the earliest events is pre-cartilage mesenchymal cell aggregation and condensation resulting from cell-cell interaction, which is mediated by cell-cell and cell-matrix adhesion (fibronectin, proteoglycans, and collagens). (DeLise A. M., Fischer L, Tuan R S, "Cellular Interactions And Signaling In Cartilage Development. *Osteoarthritis and Cartilage* 8: 309-334 (2000)). Type I collagen, the predominant matrix protein present in the early stages of development, is later transformed to Type II collagen by increased cell synthesis during differentiation. (Safronova E E, Borisova N V, Mezentseva S V, Krasnopol'skaya K D, "Characteristics Of The Macromolecular Components Of The Extracellular Matrix In Human Hyaline Cartilage At Different Stages Of Ontogenesis." *Biomedical Science* 2: 162-168 (1991)). Multiple growth factors and morphogens are also present contributing to the regulation of the differentiation process.

A few studies have demonstrated the use of MSCs for cartilage repair through intra-articular injection and have shown promise. (Murphy M, Fink D J, Hunziker E B, Barry F P, "Stem Cell Therapy In A Caprine Model Of Osteoarthritis," *Arthritis Rheumatism* 48: 3464-3474 (2003); Ponticello M S, Schinagel R M, Kadiyala, S, Barry F P, "Gelatin-Based Resorbable Spone As A Carrier Matrix For Human Mesenchymal Stem Cells In Cartilage Regeneration Therapy," *J Biomed Materials Res* 52: 246-255 (2000)). The MSCs are injected at a high cell density either alone (in saline) or in combination with a gelatinous/hydrogel matrix in order to promote cell-cell aggregation. However, the use of MSCs in combination with biomaterials of varying architectures that may closely mimic the physical architecture of the native extracellular matrix during development to direct chondrogenic differentiation has yet to be investigated.

Schwann cell-laden grafts and nerve conduits have shown promise for repairing nervous tissue (Brook G A, Lawrence J M, Raisman G. Columns of Schwann cells extruded into the CNS induce in-growth of astrocytes to form organized new glial pathways. Glia 2001; 33:118-130) and optic nerves (Negishi H. Optic nerve regeneration within artificial Schwann cell graft in the adult rat. Brain Research Bulletin 2001; 55:409-419), as have injections of adult stem cells (Desawa M. Specific induction of neuronal cells from bone marrow stromal cells and application for autologous transplantation. Journal of Clinical Investigation 2004; 113:1701-1710), but the size and complexity of the spinal cord warrants the development of specialized constructs.

The present invention addresses these problems. From a biological viewpoint, almost all human tissues and organs are characterized by well-organized hierarchical fibrous structures through the assembly of nanoscale elements. It is believed that converting biopolymers into fibers and networks that mimic native structures will ultimately enhance the utility of these materials as scaffolds. Nanoscale fibrous scaffolds may provide an optimal template for stem cell growth, differentiation, and host integration.

It is known that cells will attach to synthetic polymer scaffolds leading to the formation of tissue. (Sachlos, E. and Czernuszka, *Eur. Cells & Materials* 5: 29-40 (2003)). Using fetal bovine chondrocytes maintained in vitro, Li et al. have shown that scaffolds constructed from electrospun three-dimensional nanofibrous poly($\varepsilon$-capro-lactone) act as a biologically preferred scaffold/substrate for proliferation and maintenance of the chondrocyte phenotype. (Wan-Ju Li, et al., *J. Biomed. Mater. Res.* 67A: 1105-1114 (2003)).

Because electric polarization can influence cell growth and behavior, e.g., growth of different cell types (Yang, X. L. et al., J. Mater. Sci.: Mater. Med. 17: 767 (2006)), enhancement of nerve regeneration (Kotwal, A. et al., Biomaterials, 22: 1055 (2001)), and cell adhesion and morphology (Kapurr., et al., J. Biomed Mater. Res. 27: 133 (1996)), it was hypothesized that a three-dimensional, electrically charged polymer scaffold would be a promising approach for a number of tissue engineering applications (e.g., nerve, bone, cartilage regeneration).

SUMMARY OF THE INVENTION

In one aspect, the present invention provides an electroactive structure for growing isolated differentiable cells that comprises a three dimensional matrix of fibers formed of a biocompatible synthetic piezoelectric polymeric material wherein the matrix of fibers is seeded with the isolated differentiable cells and forms a supporting scaffold for growing the isolated differentiable cells, and wherein the matrix of fibers stimulates differentiation of the isolated differentiable cells into a mature cell phenotype on the structure. In one embodiment, the biocompatible synthetic piezoelectric polymeric material is poly (vinylidene fluoride trifluoroethylene) copolymer. In another embodiment, the matrix fibers is a non-woven mesh of nanofibers. In another embodiment, the three dimensional matrix of fibers formed of a biocompatible synthetic piezoelectric polymeric material is formed by electrospinning. In another embodiment, the isolated differentiable cells are multipotent human mesenchymal cells. In another embodiment, the human mesenchymal stem cells are isolated from human bone marrow. In another embodiment, the isolated differentiable human mesenchymal cells have a CD44+ CD34− CD45− phenotype. In another embodiment, the mature cell phenotype comprises a chondrogenic cell phenotype. In another embodiment, the chonodrogenic cell phenotype on the structure produces at least one glycosaminoglycan. In another embodiment, the mature cell phenotype comprises a neuronal cell phenotype.

In another aspect, the present invention provides a composition for use in tissue engineering that comprises (a) isolated differentiable cells, and (b) a supporting electroactive scaffold for growing the isolated differentiable cells, the supporting scaffold comprising a three dimensional matrix of fibers formed of a biocompatible synthetic piezoelectric polymeric material, wherein the matrix of fibers is seeded with the isolated differentiable cells and forms a supporting scaffold for growing the isolated differentiable cells, and wherein the matrix of fibers stimulates differentiation of the isolated differentiable cells into a mature cell phenotype on the structure. In one embodiment, the biocompatible synthetic piezoelectric polymeric material is poly (vinylidene fluoride trifluoroethylene) copolymer. In another embodiment, the three dimensional matrix of fibers is a non-woven mesh of nanofibers. In another embodiment, the three dimensional matrix of fibers formed of a biocompatible synthetic piezoelectric polymeric material is formed by electrospinning. In another embodiment, the isolated differentiable cells are multipotent human mesenchymal cells. In another embodiment, the human mesenchymal stem cells are isolated from human bone marrow. In another embodiment, the isolated differentiable human mesenchymal cells have a CD44+ CD34− CD45− phenotype. In another embodiment, the mature cell phenotype comprises a chondrogenic cell phenotype. In another embodiment, the chonodrogenic cell phenotype on the structure produces at least one glycosaminoglycan. In another embodiment, the mature cell phenotype comprises a neuronal cell phenotype.

In another aspect, the present invention provides a method of making an implantable electroactive scaffold, the method comprising the steps: (a) isolating differentiable human cells from a human donor; (b) preparing a three-dimensional matrix of fibers formed of a biocompatible synthetic piezoelectric polymeric material to form a cell scaffold; (c) seeding the cell scaffold with the isolated differentiable human cells; and (d) growing the differentiable human cells on the cell scaffold so that the differentiable human cells differentiate into a mature cell phenotype on the scaffold. In one embodiment, the differentiable human cells in step (a) are multipotent human mesenchymal cells. In another embodiment, step (a) further comprises the step of obtaining the differentiable human mesenchymal cells from bone marrow. In another embodiment, the differentiable human mesenchymal cells in step (a) have a CD44+ CD34− CD45− phenotype. In another embodiment, the biocompatible synthetic piezoelectric polymeric material in step (b) is poly (vinylidene fluoride trifluoroethylene) copolymer. In another embodiment, the three dimensional matrix of fibers in step (b) is a non-woven mesh of nanofibers. In another embodiment, the three dimensional matrix of fibers formed of a biocompatible synthetic piezoelectric polymeric material is formed by electrospinning. In another embodiment, the mature cell phenotype in step (d) comprises a chondrogenic cell phenotype. In another embodiment, the chonodrogenic cell phenotype in step (d) produces at least one glycosaminoglycan. In another embodiment, the mature cell phenotype in step (d) comprises a neuronal cell phenotype.

DETAILED DESCRIPTION OF THE INVENTION

Figure 1:
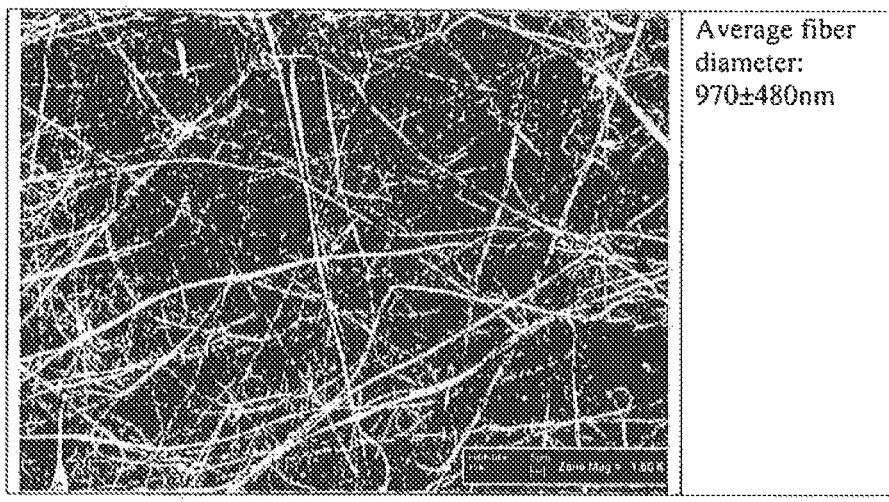
FIG. 1 shows a scanning electron micrograph (1600×) of PVDF-TrFE nanofiber mesh, average fiber diameter 970±480 nm.

The present invention provides an electroactive, or piezoelectric, biomaterial as an electroactive scaffold for repairing tissues. The piezoelectric material acts as a highly sensitive mechanoelectrical transducer that will generate charges in response to minute vibrational forces. It further provides piezoelectric compositions comprising a three-dimensional matrix of nanofibers of piezoelectric synthetic or biological polymers used as an implantable scaffolding for delivery of differentiable human mesenchymal cells in tissue engineering applications and methods of preparing them. The piezoelectric scaffolds, which demonstrate electrical activity in response to minute mechanical deformation, allow the achievement of local electric fields characteristic of the natural extracellular matrix observed during development and regeneration.

As used herein, the term "stem cells" refers to undifferentiated cells having high proliferative potential with the ability to self-renew that can migrate to areas of injury and can generate daughter cells that can undergo terminal differentiation into more than one distinct cell phenotype. These cells have the ability to differentiate into various cells types and thus promote the regeneration or repair of a diseased or damaged tissue of interest.

Specialized protein receptors that have the capability of selectively binding or adhering to other signaling molecules coat the surface of every cell in the body. Cells use these receptors and the molecules that bind to them as a way of communicating with other cells and to carry out their proper functions in the body. Each cell type has a certain combination of receptors, or markers, on their surface that makes them distinguishable from other kinds of cells.

Stem cell markers are given short-hand names based on the molecules that bind to the corresponding stem cell surface receptors. In many cases, a combination of multiple markers is used to identify a particular stem cell type. Researchers often identify stem cells in shorthand by a combination of marker names reflecting the presence (+) or absence (−) of them. For example, a special type of hematopoietic stem cell from blood and bone marrow called "side population" or "SP" is described as (CD34−/low, c-Kit+, Sca-1+).

The following markers commonly are used by skilled artisans to identify stem cells and to characterize differentiated cell types (http://stemcells.nih.gov/info/scireport/appendixE.asp, (visited 12/28/07)):

| Marker | Cell Type | Significance |
|---|---|---|
| CD34 | Hematopoietic stem cell (HSC), muscle satellite, endothelial progenitor | a highly glycosylated type I transmembrane protein expressed on 1-4% of bone marrow cells, |
| CD38 | immature T and B cells | a type II transmembrane protein found on immature T and B cells but not most mature peripheral lymphocytes |
| CD41 | platelets and megakaryocytes; | the integrin αIIb subunit |
| CD45 | WBC progenitor | the leukocyte common antigen found on all cells of hematopoietic origin |
| CD105 | Endothelial cells | a disulfide-linked homodimer found on endothelial cells but absent from most T and B cells; |
| CD133 | primitive hematopoietic progenitors | a pentaspan transmembrane glycoprotein |
| CD3 | T cells | a member of the T cell receptor complex; |
| CD4, CD8 | Mature T cells | Cell-surface protein markers specific for mature T lymphocyte (WBC subtype) |
| CD7 | Early T cells | An early T cell lineage marker, |
| CD10 | early T and B cell precursors; | a type II membrane metalloprotease |
| CD13 | granulocytes, monocytes and their precursors | a type II membrane metalloprotease, |
| CD14 | myelomonocytic lineage | a GPI-linked protein expressed mainly on myelomonocytic lineage cells; |
| CD19 | B cells | a component of the B cell antigen signaling complex; |
| CD33 | Myelomonocytic precursors | a sialic acid binding protein absent from pluripotent stem cells that appears on myelomonocytic precursors after CD34; |

| Marker | Cell Type | Significance |
| --- | --- | --- |
| CD38 | WBC lineages | A Cell-surface molecule that identifies WBC lineages. Selection of CD34+/CD38− cells allows for purification of HSC populations |
| CD44 | Mesenchymal | A type of cell-adhesion molecule used to identify specific types of mesenchymal cells |
| CD56 | NK cells | an isoform of the neural adhesion molecule found exclusively on natural killer (NK) cells; |
| CD127 | lymphocytes | the high affinity interleukin 7 receptor expressed on lymphocytes; |
| CD138 | Immature B cells and plasma cells | an extracellular matrix receptor found on immature B cells and plasma cells; |
| Glycophorin A | RBCs, embryoid precursors | a sialoprotein present on human RBCs and embryoid precursors; |
| CD90 | prothymocytes | a GPI-cell anchored molecule found on prothymocyte cells in humans. |
| c-kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Fetal liver kinase-1 (Flk-1) | endothelial | Cell-surface receptor protein that identifies endothelial cell progenitor; marker of cell-cell contacts |

The term "cellular differentiation" as used herein refers to the process by which cells acquire a cell type.

The term "chondrocytes" as used herein refers to cells found in cartilage that produce and maintain the cartilaginous matrix. From least to terminally differentiated, the chondrocytic lineage is (i) Colony-forming unit-fibroblast (CFU-F); (ii) mesenchymal stem cell/marrow stromal cell (MSC); (iii) chondrocyte. The term "chondrogenesis" refers to the formation of new cartilage from cartilage forming or chondrocompetent cells.

The term "ΔHf" refers to Heat of Fusion.

The term "nanoscale fiber" generally refers to fibers whose diameter ranges from about 1 to about 1000 nanometers.

The term "progenitor cell" as used herein refers to an immature cell in the bone marrow that can be isolated by growing suspensions of marrow cells in culture dishes with added growth factors. Progenitor cells are referred to as colony-forming units (CFU) or colony-forming cells (CFC). The specific lineage of a progenitor cell is indicated by a suffix, such as, but not limited to, CFU-F (fibroblastic).

As used herein, the terms "osteoprogenitor cells," "mesenchymal cells," "mesenchymal stem cells (MSC)," or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

The term "piezoelectric material" as used herein refers to any material that exhibits piezoelectric properties or effects. The terms "piezoelectric properties" or "piezoelectric effects" are used interchangeably to refer to the property exhibited by piezoelectric materials of becoming electrically polarized when mechanically strained and of becoming mechanically strained when an electric field is applied.

The term PLLA as used herein refers to biodegradable aliphatic polyester homopolymer poly L-lactic acid (PLLA) obtained from Alkermes, Inc.

The present invention described hereinabove has both human and veterinary utility. The term "subject" as used herein therefore includes animals of mammalian origin, including humans.

The term "Tm" refers to melting point.

The terms "Transforming Growth Factor", "tumor growth factor" or "TGF" are used interchangeably to describe two classes of polypeptide growth factors, TGFα and TGFβ. TGFα, which is upregulated in some human cancers, is produced in macrophages, brain cells, and keratinocytes, and induces epithelial development. TGFβ exists in three known subtypes in humans, TGFβ1, TGFβ2, and TGFβ3 that are upregulated in some human cancers, and play crucial roles in tissue regeneration, cell differentiation, embryonic development, and regulation of the immune system. TGFβ receptors are single pass serine/threonine kinase receptors.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are neither intended to limit the scope of what the inventors regard as their invention nor they intended to represent that the experiments below are all or the only experiments performed.

Example 1. Fabrication of Piezoelectric Tissue Engineering Scaffolds

The present invention makes use of fibers formed from a permanently piezoelectric poly (vinylidene fluoride trifluoroethylene) (PVDF-TrFE) copolymer. The PVDF-TrFE copolymer was fabricated into a nanofibrous scaffold using an electrospinning technique.

The electrospinning process is affected by varying the electric potential, flow rate, solution concentration, capillary-collector distance, diameter of the needle, and ambient parameters like temperature. PVDF-TrFE and PLLA were electrospun into fibers according to commonly used optimization procedures whereby porosity, surface area, fineness and uniformity, diameter of fibers, and the pattern thickness of the sheet could be manipulated. See, e.g., Greiner, A. et al Angew Chem. Int. Ed. Engl. 46: 5670 (2007).

The electrospinning setup used herein is described in U.S. patent application Ser. No. 11/291,701, which is incorporated herein by reference. It is comprised a syringe pump containing a 13-20 gauge needle mounted on a robotic arm in order to control the splaying of fibers on the collector. An electrically grounded stainless steel plate of dimensions 15×30 cm is used as the collector.

PVDF-TrFE copolymer (65/35) purchased from Solvay Solexis, Inc. (NJ, USA) was dissolved in Methylethylketone (MEK). For the successful formation of fibers, a 15% w/v solution concentration of the polymer in MEK was used. The syringe pump was filled with the polymer solution, and a constant flow rate of 0.035 ml/min was maintained using the syringe pump. The positive output lead of a high voltage power supply (Gamma High Voltage, Inc.) was attached to a 20 gauge needle, and a 25 kvolt voltage was applied to the solution. The collector-to-needle distance was 18.5 cm. The electrospinning process was performed in about 12% to about 13% humidity at 25 degrees C. When the charge of the polymer at increasing voltage exceeded the surface tension at the tip of the needle, the polymer splayed randomly as fibers. These were collected as nonwoven mats on the grounded plate.

Example 2. Characterization of the Electrospun PVDF-TrFE Fibers

Structure and piezoelectric activity were examined by differential scanning calorimetry (DSC), thermogravimetric analysis (TGA), thermally stimulated current (TSC) spectroscopy, X-ray diffraction (XRD) and fourier transform infrared spectroscopy (FTIR). Comparisons were made between PVDF-TrFE polymer powder and electrospun PVDF-TrFE fibers.

The fiber diameter of electrospun PVDF-TrFE fibers was characterized using Scanning Electron Microscopy (SEM) according to established methods and compared to poly L-lactic acid (PLLA) meshes. FIG. 1 shows that the resulting fibrous meshes had an average fiber diameter of 970±480 nm, with uniform fiber morphologies having no beading, as characterized by scanning electron microscopy. The fiber mats were free of droplets.

Thermally stimulated current (TSC) spectroscopy is widely used to understand dielectric relaxation in complex solid systems. TSC is based on the ability of polar molecules to be moved by an electric static field. At a temperature $T_p$, an electric field is applied during a time $t_p$ long enough to let the dipoles orient themselves. This configuration is fixed by a rapid decrease in temperature to reach a temperature $T_0$. At $T_0$, the sample is short-circuited during a time $t_0$ to remove the space charges and to equilibrate the temperature. The progressive and sequential release of the entities oriented previously can be observed during a linear rise in temperature. The depolarization current is then recorded as a function of the temperature.

Figure 2:
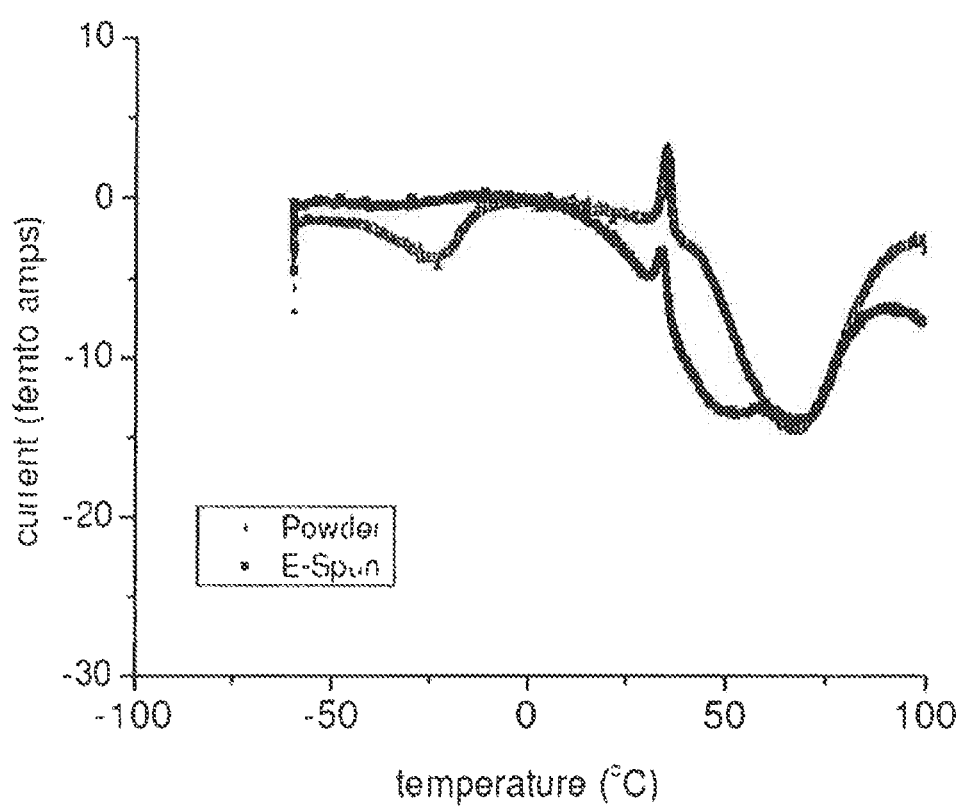
FIG. 2 shows TSC analysis of PVDF-TrFE powder and electrospun PVDF-TrFE mat (externally applied field: 100V).

TSC measurements confirmed that the electrospun PVDF-TrFE fiber scaffolds have internal charges comparable to the original piezoelectric polymer powder. The electrospun and powder forms were heated from −60° C. to 140° C. (7 C per min) and were subjected to an externally applied field of 100 V. FIG. 2 shows the data resulting from TSC analysis of the electrospun PVDF-TrFE mat and the non-processed powder form. It shows that for both the powder and electrospun forms, there was polarization due to the applied electric field followed by a spontaneous relaxation.

Thermal Gravimetric Analysis (TGA) was performed to detect any remaining solvent in the nanofiber mat using a Thermal Gravimetric Analyzer (TA Instrument model Q50). The analyzer measures weight changes in materials with regard to temperature, which allows for the effective quantitative analysis of thermal reactions that are accompanied by mass changes resulting from dehydration, decomposition and oxidation of a sample.

The nanofiber mat was subjected to vacuum prior to the analysis. A sample of the test material was placed into a high alumina cup supported on, or suspended from, an analytical balance located outside the furnace chamber. The balance was zeroed, and the sample cup heated according to a predetermined thermal cycle. The balance sends the weight signal to the computer for storage, along with the sample temperature and the elapsed time. The TGA curve plots the TGA signal, converted to percent weight change, on the Y-axis against the reference material temperature on the X-axis.

The results showed that fibrous meshes with vacuum treatment had a 0.5% solvent content as demonstrated by a loss of 0.5 weight percent as compared to the unprocessed/raw polymer.

Results obtained by DSC, XRD and FTIR showed that the electrospinning process did not alter significantly the polymer structure compared to the original piezoelectric polymer powder.

Differential scanning calorimetry (DSC) is used to study the thermal behavior of polymers. In this technique, separate chambers for the sample and reference are heated equally. Transformations taking place in the sample are detected by the instrument, which compensates by changing the heat input so that there is a zero temperature difference between the reference and sample. The amount of electrical energy supplied to the heating elements is then proportional to the heat released by the sample. Thermal analysis was performed with a TA Model Q100 Differential Scanning calorimeter.

Fourier-Transform Infrared Spectroscopy (FTIR) is used to observe vibrational changes in chemical bonds. Here, infrared radiation in the range from 4000 to 600 cm-1, the mid-infrared region, was used. The presence and intensity of specific vibrational frequencies allows for determination of functional groups in organic molecules. The class of material (proteinaceous, cellulosic, and so forth) then can be identified from these functional groups.

A micro x-ray diffractometer capable of focusing a collimated x-ray beam (20 to 800 micron diameter range) onto areas of interest within the sample was used to generate an x-ray diffraction (XRD) pattern characteristic for the crystalline phases contained within the sample. X-rays diffracted by the sample strike a detector and are converted to an electronic signal that is then further processed by software. Search-match software then was used to match the unknown diffraction pattern to a database of diffraction patterns collected from reference compounds.

The degree of crystallinity was determined, and the piezoelectric crystal form of the copolymer present in the electrospun PVDF-TrFE mats was confirmed, by DSC. Comparisons of PVDF-TrFE mats with the piezoelectric unprocessed powder and solvent-cast film as well as with nonpiezoelectric-unpoled PVDF pellets were made.

TABLE 1

Comparison of DSC data with literature values

|  | PVDF | PVDF-TrFE (65/35) | PVDF-TrFE (65/35) | PVDF-TrFE (65/35) |
|---|---|---|---|---|
| Physical form | Pellet | Powder | Solvent-cast film | Electrospun fiber |
| Tm (C.) | 171 (161*) | 107 (1 peak) | 115 (1 peak) | 115 (1 peak) |
|  |  | 147 (154.55**) (2 peak) | 147 (2 peak) | 149 (2 peak) |
| ΔHf (J/g) | 45 (50*) | 13 (1 peak) | 13 (1 peak) | 15 (1 peak) |
|  |  | 23 (30**) (2 peak) | 34 (2 peak) | 28 (2 peak) |

*Zhao, Z. et al., J. Appl. Polym. Sci. 97: 466-74 (2005);
**Data provided by supplier (Solvay Solexis, Inc.)

Table 1, which compares the experimental DSC data with literature values for test polymers (in parentheses), shows that low and high temperature peaks were observed in the PVDF-TrFE polymer during the first and second heating cycle. The differences in the first heating cycle between the test polymers were not detectable in the second heating cycle, which suggests that there is no chemical degradation or changes in the chemical structure due to the fabrication process. The melting points and heats of fusion for PVDF-TrFE materials are distinct from values obtained for the unpoled PVDF pellet, indicating that the piezoelectric beta-phase crystal form is present in the electrospun mat.

Moreover, the electrospun electroactive PVDF-TrFE fibers of the present invention do not require poling to show a piezoelectric effect. The term "poling" as used herein refers to the adjustment of the polarity of a substance. For example, electric dipoles may be aligned (meaning arranged, positioned or synchronized in a manner that allows for proper or optimal functioning) by utilizing an electric field. The term "polarity" refers to the property, state or condition of having or manifesting two opposite or opposing charges within the same body.

Figure 3:
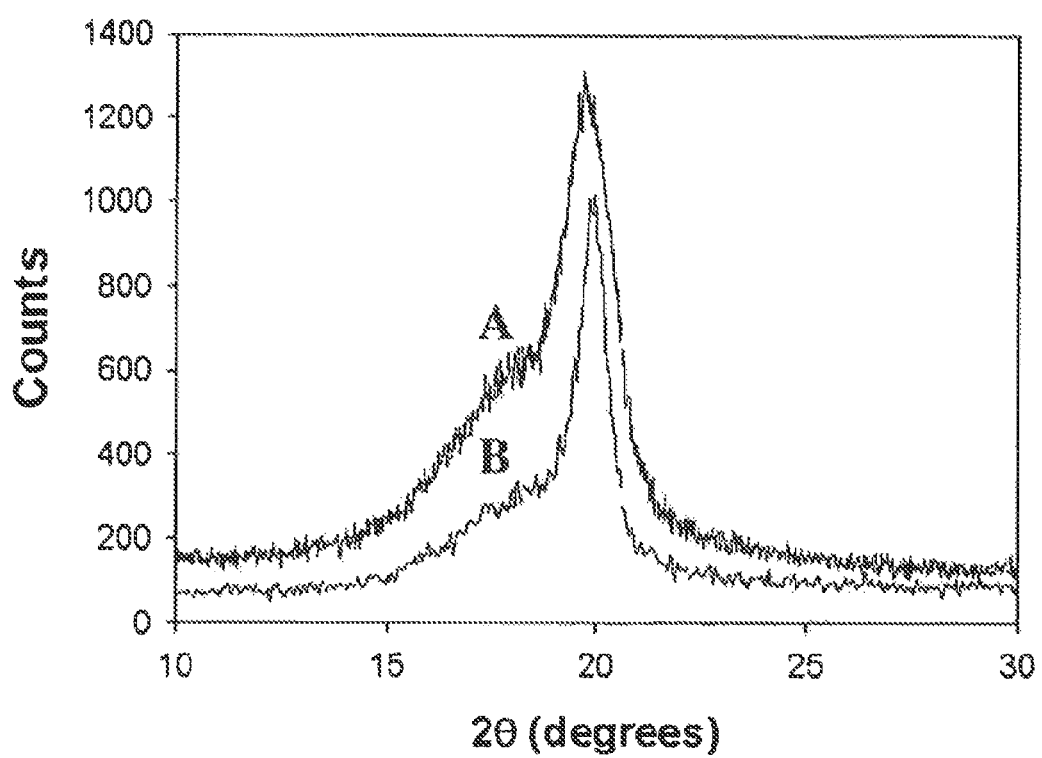
FIG. 3 shows data resulting from X-ray diffraction analysis of PVDF-TrFE (A) electrospun nanofibers; (B) raw/unprocessed PVDF-TrFE powder.
Figure 4:
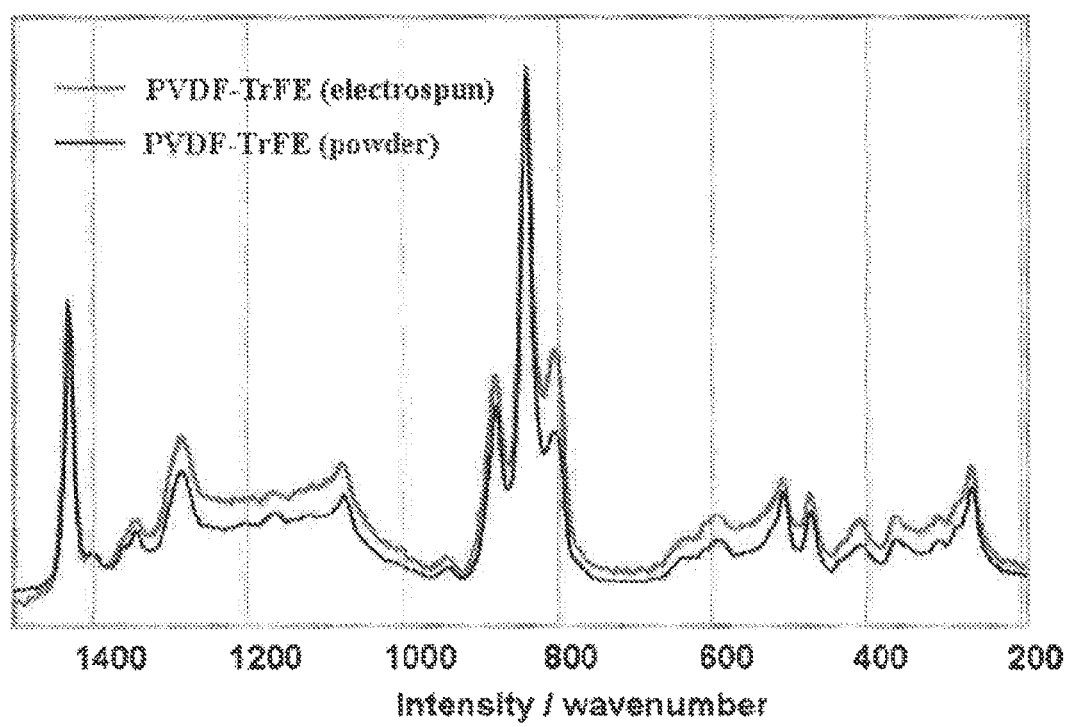
FIG. 4 shows FTIR analysis of PVDF-TrFE powder (gray line) and electrospun PVDF-TrFE mat (black line).

FIG. 3 shows X-ray diffractograms of (A) electrospun; and (B) non-processed powder form of PVDF-TrFE. FIG. 4 shows FTIR analysis of PVDF-TrFE powder (gray line) and electrospun PVDF-TrFE mat (black line). Together, XRD and FTIR analysis confirmed the presence of the poled, piezoelectric phase (beta-crystal phase) in the electrospun PVDF-TrFE. FIG. 4 shows that unprocessed and electrospun mats have similar FTIR spectra.

Example 3. PVDF-TrFE Fiber Mats Support Stem Cells

Three studies were conducted to establish that the PVDF-TrFE fiber mesh can be used as a scaffold to support stem cells or other cell types Materials and Methods
1. Cells
(a) Cell Line Model for Neuronal Differentiation.
When treated with nerve growth factor (NGF), PC12 cells, a cell line derived from a pheochromocytoma of the rat adrenal medulla, stop dividing, grow long neurites, and undergo terminal differentiation, which makes this cell line a useful model system for neuronal differentiation.

PC12 cells (ATCC number CRL-1721) were seeded at $3\times10^3$ cells per cm2 culture dish and maintained in ATCC formulated F-12K medium containing 1.5% fetal bovine serum and 15% horse serum. Cultures were maintained at 37 C, 95% air, 5% $CO_2$ atmosphere. For induction of the neuronal phenotype, 50 ng/ml NGF (Chemicon) was added to the medium at the start of the culture and maintained throughout the duration of the culture. The term "induction media" refers to the medium containing NGF.

(b) Fibroblasts.

Normal human skin fibroblasts (ATCC number SCRC-1041) were seeded at $5\times10^3$ cells per cm2 culture dish and maintained in Dulbecco's modified Eagle's medium containing 15% fetal bovine serum.

(c) Mesenchymal Stem Cells.

Human mesenchymal stem cells (hMSCs) were prepared as described in Livingston, et al., J. Materials Science: Materials in Med. 14: 211-218 (2003) and in U.S. Pat. No. 5,486,359, which are incorporated herein by reference. In brief, bone marrow aspirates of 30-50 mL were obtained from healthy human donors. Marrow samples were washed with saline and centrifuged over a density cushion of ficoll. The interface layer was removed, washed, and the cells counted. Nucleated cells recovered from the density separation were washed and plated in tissue culture flasks in Dulbecco's Modified Eagle's Medium (DMEM) containing 10% fetal bovine serum ("FBS", HyClone Laboratories, Inc.). Non-adherent cells were washed from the culture during biweekly feedings. Colony formation was monitored for a 14-17 day period. MSC's were passaged when the tissue culture flasks were near confluent. At the end of the first passage, MSCs were enzymatically removed from the culture flask using trypsin-EDTA and replated at a lower density for further expansion. At the end of the second passage, MSC's were either seeded onto scaffolds or cryopreserved until future use.

The hMSC cells were identified as multipotent stem cells based on surface marker characterization, which distinguishes the stem cells from other cell types in the bone marrow, for example white blood cells. Cells expressing CD44 (CD44+) and the absence of CD45 (CD45−) and CD34 (CD34−) surface antigens were verified by fluorescence-activated-cell-sorter.

Chondrogenic differentiation of hMSCs was performed according to published procedures. See Barry, F. et al., Exp. Cell Res. 268, 189 (2001), which is incorporated herein by reference. $2\times10^5$ cells were seeded on PVDF-TrFE scaffolds in 24-well plates using three different culture media: (i) the chondrogenic culture media containing TGFb3, or induction media, (CCM+), consisted of 1 mM sodium pyruvate (Sigma), 0.1 mM ascorbic acid-2-phosphate (Wako), $1\times10^{-7}$ M dexamethasone (Sigma), 1% ITS1 (Collaborative Biomedical Products), and 10 ng/ml recombinant human TGF-β3 (Oncogene Sciences) dissolved in Dulbecco's Modified Eagle's Medium containing 4-5 g/L glucose (DMEM-LG), (ii) chondrogenic culture media (CCM) without TGFβ3 (CCM−); (iii) mesenchymal stem cell growth media (MSCGM), the standard growth media for hMSCs, consisting of DMEM-LG with 10% fetal bovine serum and 1% antibiotic-antimycotic. Cells were harvested after 1, 14, and 28 days of culture.

Cell pellet cultures served as controls for these experiments. A single cell pellet was produced by centrifuging 2.5×105 cells in a 15 mL centrifuge tube and culturing the pelleted cells in the tube.

Cell Viability:

Metabolic activity and cell growth were measured using the XTT kit (Biotium, USA). XTT is a tetrazolium derivative that measures cell viability based on the activity of mitochondria enzymes in live cells that reduce XTT and are inactivated shortly after cell death. XTT is reduced to a highly water-soluble orange colored product, the amount of which is proportional to the number of living cells in the sample, and can be quantified by measuring absorbance at wavelength of 475 nm.

Cells were plated onto scaffolds in 96-well tissue culture plates at 10,000 cells per well for up to 7 days. Reagents were added such that the final volume of tissue culture medium (containing 10% FBS) in each well was 0.1 mL. For one 96-well plate, 25 µL Activation Reagent was mixed with 5 mL XTT Solution to derive activated XTT solution. 25 µL or 50 µL of the activated XTT solution was added to each well and the plate incubated in an incubator for 4 hours. The plate was shaken gently to evenly distribute the dye in the wells. The absorbance of the samples was measured spectrophotometrically at a wavelength of 450-500 nm. Reference absorbance is measured at a wavelength of 630-690 nm.

Real Time Reverse Transcriptase-Polymerase Chain Reaction (RT-PCR):

RNA was isolated using a Qiagen Mini kit (Qiagen). Samples were lysed and then homogenized using QiaShredder columns (Qiagen). Ethanol was added to the lysate and the lysate was loaded onto the RNeasy silica-gel membrane. Pure, concentrated RNA then was eluted from the membrane in water.

Relative gene expression analysis (QuantiTect SYBR Green RT-PCR kit, Qiagen) for chondrogenic markers (chondroadherin, type II collagen), and focal adhesion kinase (FAK) was performed using the MX4000 detection system (Stratagene). Ribosomal protein, large, P0 ("RPLPO") was used as housekeeping gene.

Qiagen PCR Kit:

2× QuantiTect SYBR Green RT-PCR Master Mix (stored at −20° C.), template RNA, primers, and RNase-free water were thawed, mixed individually and placed on ice. A reaction components master mix was prepared as follows:

| Component | Volume/reaction | Final concentration |
|---|---|---|
| 2x QuantiTect SYBR Green RT-PCR Master Mix | 12.5 µl | 1x |
| Primer A | Variable | 0.5-2.0 µM |
| Primer B | Variable | 0.5-2.0 µM |
| QuantiTect RT Mix | 0.25 µl | 0.25 µl |
| RNAse-free water | Variable | — |
| Optional: Uracil-N-glycolase, heat labile | Variable | 1-2 units/reaction |
| Template RNA | Variable | ≤500 ng/reaction |
| Total volume | 25 µl | |

Where final reaction volumes other than 25 µl were used, the volumes of 2× Quanti-Tect SYBR Green RT-PCR Master Mix and Quanti Tect RT Mix used were adjusted so that the ratio between them remained constant.

The master mix was mixed thoroughly and appropriate volumes dispensed into PCR tubes. Template RNA (≤500 ng/reaction) was added to the individual PCR tubes and incubated on ice for less than 30 min. The MX4000 was programmed and data acquisition performed during the extension step. A melting curve analysis of the RT-PCR product(s) between 55 C and 95 C was performed to verify specificity and identify of the RT-PCR products.

A standard curve was generated using various RNA concentrations, which contain substantial levels of chondrogenic markers (chondroadherin, type II collagen) and focal adhesion kinase (FAK). Two optical channels, one for SYBR Green and one for a reference dye (ROX), were used to correct for volume and plate location differences. Each template was analyzed in triplicate. Stratagene reaction tubes (Cat. No. 41002) and caps (Cat. No. 410024) were used, and fluorscence data was collected for SYBR Green. A typical thermal profile used was the following:

50 C for 30 min (reverse transcriptase step)
95° C. for 15 min (to activate the DNA polymerase)
40 cycles of:
94° C. for 15 sec
55° C. for 30 sec
72° C. for 30 sec (triplicate readings of fluorescence were taken during this phase of the cycle.)

A dissociation curve was generated after the amplification cycles were completed. For the amplification plots, fluorescence was analyzed as "dRn" to generate Ct values for all of the samples simultaneously. Gene expression levels were analyzed according to Mueller (Mueller, P. Y., Janoviak, H., Miserez, A. R., Dobbie, Z., Biotechniques 32, 1372-74 (2002)), which is incorporated herein by reference, and expressed as "mean normalized expression."

Confocal fluorescence microscopy was used to obtain fluorescence images of cells cultured on fiber scaffolds. A fluorescent stain, which visualizes nuclear DNA (4',6-diamidino-2-phenylindole, DAPI, Invitrogen, USA) and the actin cytoskeleton (Alexa Fluor 488 phalloidin; Invitrogen, USA) in fixed cells was used. Fluorescence images of cells cultured on fiber scaffolds were taken with a confocal fluorescence microscope (Clsi, Nikon, Japan).

Cell Proliferation.

Cell number over time was measured using the PicoGreen assay (Invitrogen).

sGAG Synthesis:

Absorbance at 656 nm was used to measure total sulfated proteoglycan content ("sGAG") using the Blycan assay (Biodyne Science, UK).

Results

The results show that PDVF-TrFE fiber piezoelectric scaffolds are biocompatible and stimulate differentiation of hMSCs into chondrocytes, PC-12 neuronal cells into neurites; and stimulate attachment and growth of fibroblasts on the PVDF-TrFE scaffold as compared to growth of these cells under normal culture conditions.

Figure 5A:
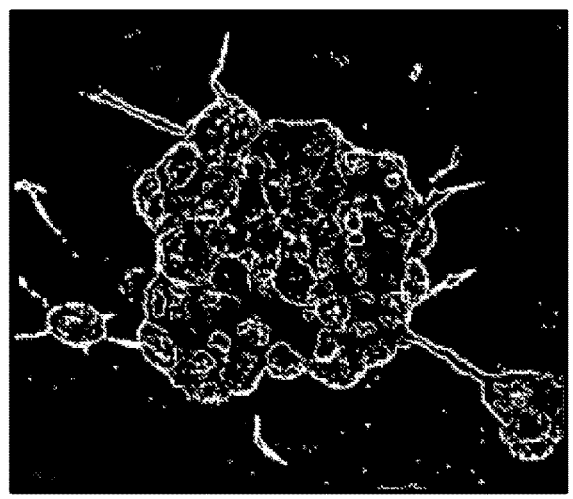
FIG. 5A shows confocal image of PC-12 cells cultured on PVDF-TrFE meshes in induction media.
Figure 5B:
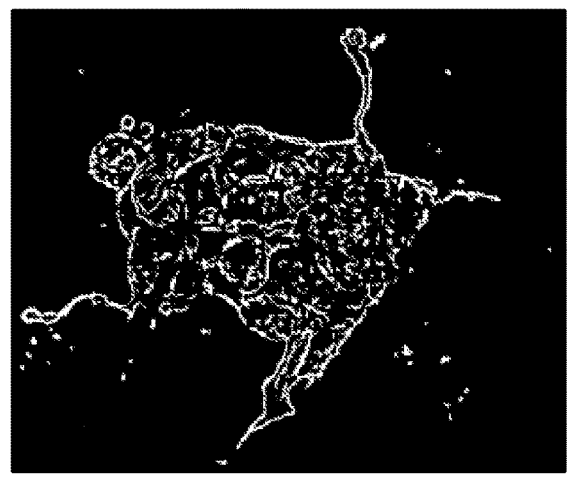
FIG. 5B shows confocal image of PC-12 cells cultured in standard growth media.
Figure 5C:
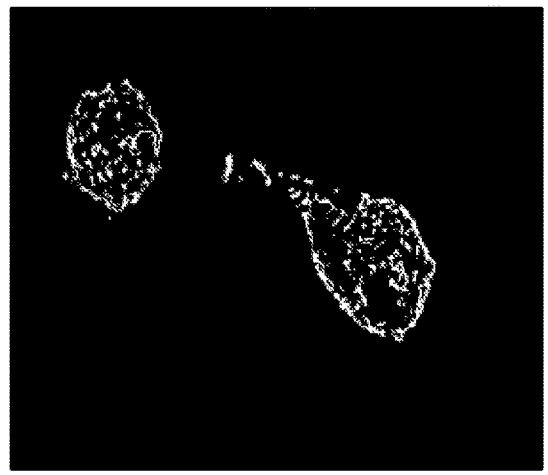
FIG. 5C shows confocal image of PC-12 cells on PLLA meshes in induction media (60× objective D)
Figure 5D:
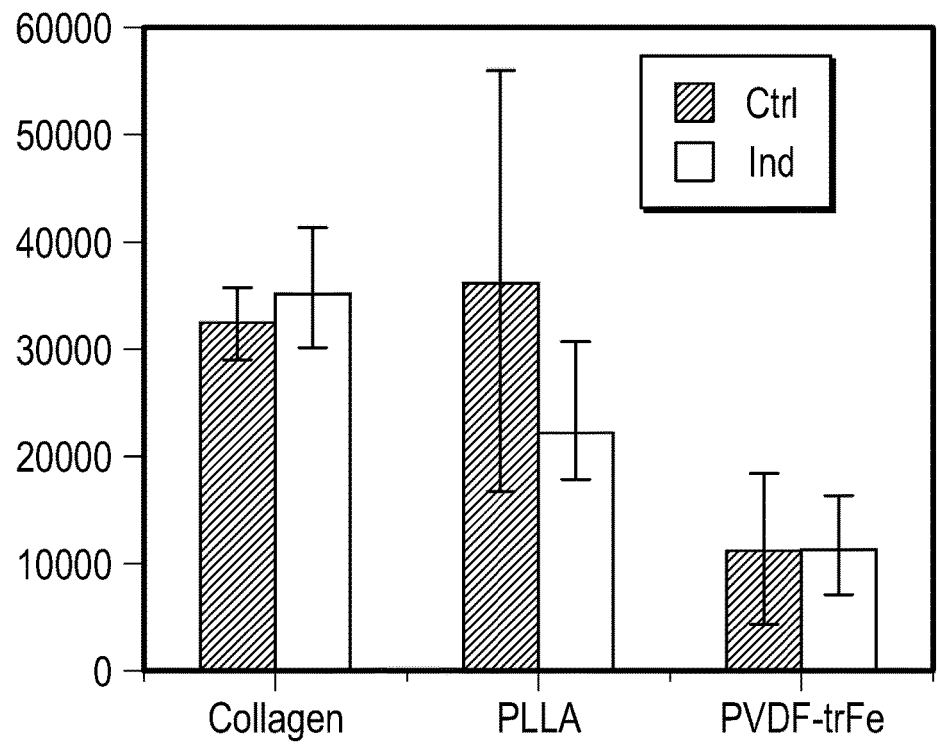
FIG. 5D is a graph showing metabolic activity of PC-12 cells at 10 days in culture *P<0.05 for PVDF-TrFE versus collagen.

FIGS. 5A-5C show that at 10 days in culture, extensive neurite extension on PVDF-TrFE meshes was seen with or without media containing Nerve Growth Factor (NGF). Neurite extension of cells grown on electro spun poly-L-lactic acid [PLLA] (average fiber diameter of 1.0+/−0.4 µm) scaffolds appeared less extensive and only occurred in the presence of NGF. As shown in FIG. 5D, cell growth, as measured by metabolic activity using the XTT kit (Biotium, USA), was significantly lower on PVDF-TrFE meshes for both growth and induction media as compared to tissue culture polystyrene and PLLA scaffolds, suggesting that PVDF-TrFE downregulates proliferation and facilitates differentiation.

Figure 6:
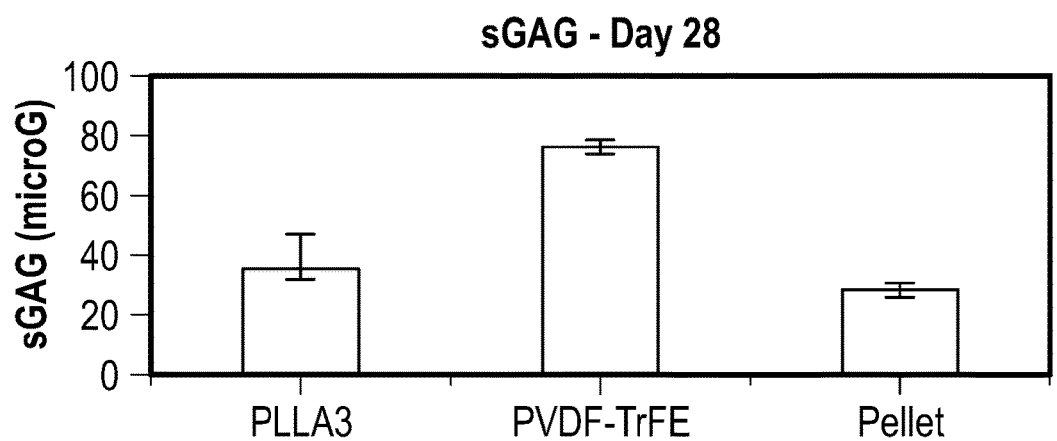
FIG. 6 shows chondroadherin and focal adhesion kinase (FAK) gene expression in human mesenchymal stem cells (hMSCs) cultured for 28 days on PLLA and PVDF-TrFE scaffolds. Cell pellet cultures serve as controls.
Figure 7:
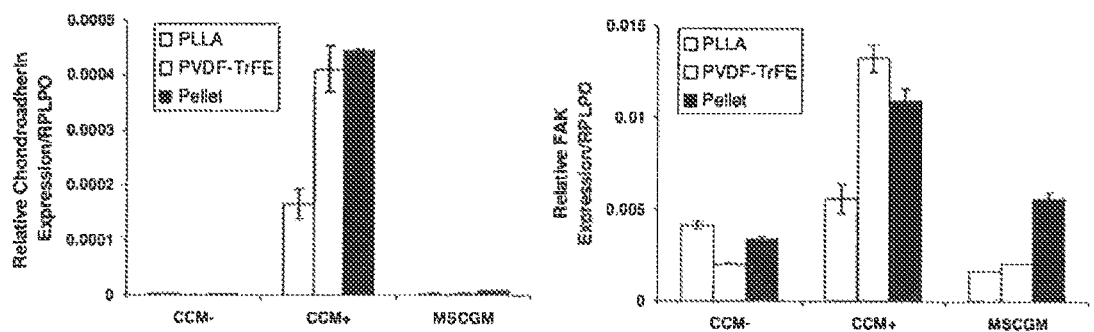
FIG. 7 shows glycosaminoglycan production (sGAG) for human mesenchymal stem cells cultured in chondrogenic induction media on PLLA and PVDF-TrFE meshes at 28 days. Pellet cultures served as a positive control. *p<0.05.

FIGS. 6 and 7 shows that for human mesenchymal stem cell chondrogenesis, glycosaminoglycan production by cells on PVDF-TrFE meshes/mats was significantly higher than for cells on PLLA or in pellet culture (positive control) in inductive media. It is known that transforming growth factor β (TGF-β) induces chondrogenesis in hMSCs and involves deposition of a cartilage-specific extracellular matrix. Barry, F. et al., Exp. Cell Res. 268, 189 (2001). Initial studies showed that chondrogenic markers and sGAG synthesis was significantly induced by CCM+ media. As shown in FIG. 6, the sGAG concentrations and chondroadherin/FAK gene expression was significantly higher on PVDF-TrFE as compared to PLLA scaffolds ($p<0.01$). However, no significant differences between PVDF-TrFE and PLLA scaffolds could be seen using CCM- and MSCGM media (chondroadherin, type II collagen, and FAK gene expression; sGAG synthesis).

Figure 8:
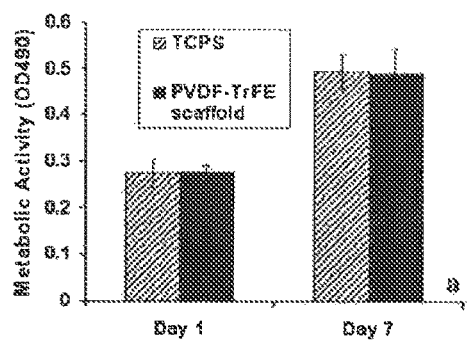
FIG. 8 shows (a) viability and growth of human skin fibroblasts on electrospun PVDF-TrFE fiber scaffold compared to tissue culture polystyrene (TCPS); (b) SEM image of electrospun PVDF-TrFE fibers.
Figure 8:
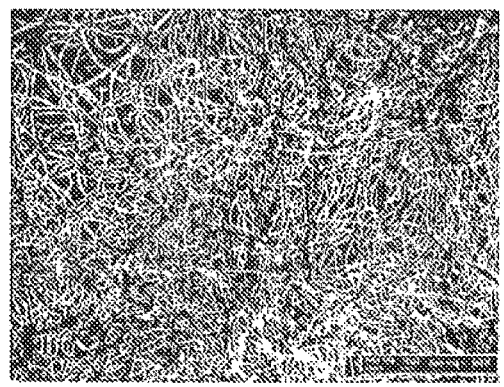
Figure 9:
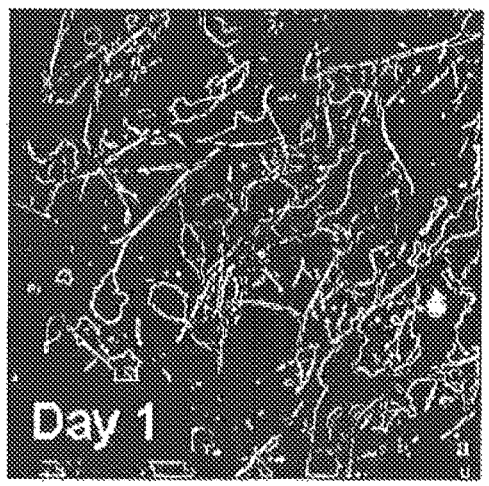
FIG. 9 shows confocal scanning laser microscopy images of human skin fibroblasts attached to PVDF-TrFE fibers after 1 day and after 7 days of cell culture.
Figure 9:
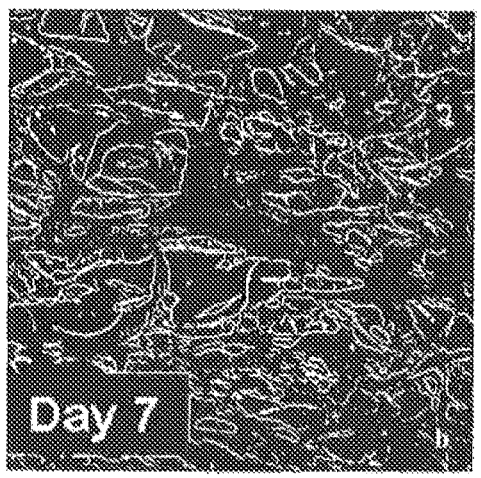

Human skin fibroblasts (ATCC number SCRC-1041) were cultured on PVDF-TrFE fiber scaffolds over a 7-day period. Tissue culture polystyrene (TCPS) served as the control). FIG. 8 and FIG. 9 show that fibroblasts grew and were well-spread on PVDF-TrFE meshes. This was comparable to growth on tissue culture plastic (positive control).

Confocal fluorescence microscopy verified the attachment and proliferation of the cells on the PVDF-TrFE fiber scaffolds. FIG. 9 shows confocal scanning laser microscopy images of human skin fibroblasts attached to PVDF-TrFE fibers after 1 day and after 7 days of cell culture. The cell morphologies of one day cultures on the fiber scaffolds are distinctly different from those of 7-day cultures. On day 1, the cells are not fully spread out. When grown on the scaffolds for a longer time (7 days) cells exhibit a more elongated and spread-out morphology.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. An electroactive structure comprising:
   a three dimensional matrix of electrospun fibers for growing isolated differentiable cells, the three dimensional matrix of fibers formed of a biocompatible synthetic permanently piezoelectric polymeric material;
   a growth factor capable of promoting the differentiation of the cells;
   wherein the matrix of fibers is seeded with the isolated differentiable cells and forms a supporting scaffold for growing the isolated differentiable cells, and
   wherein the matrix of fibers stimulates differentiation of the isolated differentiable cells into a mature cell phenotype on the supporting scaffold;
   wherein the biocompatible synthetic piezoelectric polymeric material is poly(vinylidene fluoride trifluoroethylene) copolymer;
   wherein at least a portion of the copolymer is in a beta-phase crystal form;
   wherein the isolated differentiable cells are multipotent human mesenchymal cells;
   wherein it is not required to adjust the polarity of the electrospun fibers for the electrospun fibers to display a piezoelectric effect; and
   wherein each fiber of the three dimensional matrix of electrospun fibers: (i) has a fiber diameter of about 1 nm to about 1,000 nm, (ii) has a uniform fiber morphology with no beading, and (iii) is free of droplets.

2. The electroactive structure according to claim 1, wherein the matrix of fibers is a non-woven mesh of nanofibers.

3. The electroactive structure according to claim 1, wherein the isolated differentiable human mesenchymal cells are isolated from human bone marrow.

4. The electroactive structure according to claim 1, wherein the isolated differentiable human mesenchymal cells have a CD44+ CD34− CD45− phenotype.

5. The electroactive structure according to claim 1, wherein the mature cell phenotype comprises a chondrogenic cell phenotype.

6. The electroactive structure according to claim 5, wherein the chonodrogenic cell phenotype produces at least one glycosaminoglycan.

7. A composition for use in tissue engineering, comprising:
   (a) isolated differentiable cells,
   (b) a supporting electroactive scaffold for growing the isolated differentiable cells, the supporting scaffold including a three dimensional matrix of electrospun fibers formed of a biocompatible synthetic permanently piezoelectric polymeric material; and
   (c) a growth factor capable of promoting the differentiation of the cells;
   wherein the matrix of fibers is seeded with the isolated differentiable cells and forms a supporting scaffold for growing the isolated differentiable cells, and
   wherein the matrix of fibers stimulates differentiation of the isolated differentiable cells into a mature cell phenotype on the supporting scaffold;
   wherein the biocompatible synthetic piezoelectric polymeric material is poly(vinylidene fluoride trifluoroethylene) copolymer;
   wherein at least a portion of the copolymer is in a beta-phase crystal form;
   wherein the isolated differentiable cells are multipotent human mesenchymal cells;
   wherein it is not required to adjust the polarity of the electrospun fibers for the electrospun fibers to display a piezoelectric effect; and
   wherein each fiber of the three dimensional matrix of electrospun fibers: (i) has a fiber diameter of about 1 nm to about 1,000 nm, (ii) has a uniform fiber morphology with no beading, and (iii) is free of droplets.

8. The composition according to claim 7, wherein the three dimensional matrix of fibers is a non-woven mesh of nanofibers.

9. The composition according to claim 7, wherein the isolated differentiable human mesenchymal cells are isolated from human bone marrow.

10. The composition according to claim 7, wherein the isolated differentiable human mesenchymal cells have a CD44+ CD34− CD45− phenotype.

11. The composition according to claim 7, wherein the mature cell phenotype comprises a chondrogenic cell phenotype.

12. The composition according to claim 11, wherein the chonodrogenic cell phenotype produces at least one glycosaminoglycan.

* * * * *